United States Patent
Andresen et al.

(10) Patent No.: US 11,058,780 B2
(45) Date of Patent: Jul. 13, 2021

(54) PALPABLE MARKER COMPOSITION

(71) Applicants: TECHNICAL UNIVERSITY OF DENMARK, Lyngby (DK); NANOVI RADIOTHERAPY APS, Lyngby (DK)

(72) Inventors: Thomas Lars Andresen, Vanlose (DK); Rasmus Irming Jølck, Kgs. Lyngby (DK); Linda Maria Bruun, Copenhagen S (DK)

(73) Assignees: TECHNICAL UNIVERSITY OF DENMARK, Lyngby (DK); NANOVI RADIOTHERAPY APS, Lyngby (DK)

( * ) Notice: Subject to any disclaimer, the term of this patent is extended or adjusted under 35 U.S.C. 154(b) by 32 days.

(21) Appl. No.: 16/302,517

(22) PCT Filed: May 19, 2017

(86) PCT No.: PCT/EP2017/062181
§ 371 (c)(1),
(2) Date: Nov. 16, 2018

(87) PCT Pub. No.: WO2017/198858
PCT Pub. Date: Nov. 23, 2017

(65) Prior Publication Data
US 2019/0275174 A1 Sep. 12, 2019

(30) Foreign Application Priority Data

May 20, 2016 (SE) .................................... 1650695-8

(51) Int. Cl.
*A61K 49/00* (2006.01)
*A61K 9/00* (2006.01)
*A61K 47/26* (2006.01)

(52) U.S. Cl.
CPC ........ *A61K 49/0052* (2013.01); *A61K 9/0024* (2013.01); *A61K 47/26* (2013.01)

(58) Field of Classification Search
CPC .. A61K 49/0052; A61K 47/26; A61K 9/0024; A61K 49/0054; A61K 49/0073; A61K 49/226; A61K 51/0491; A61K 51/1213; A61K 2123/00
See application file for complete search history.

(56) References Cited

U.S. PATENT DOCUMENTS

| | | | |
|---|---|---|---|
| 3,678,152 A | 7/1972 | Bjork et al. | |
| 3,763,226 A | 10/1973 | Ingelman | |
| 3,763,227 A | 10/1973 | Ingelman | |
| 3,804,892 A | 4/1974 | Ingelman | |
| 3,852,341 A | 12/1974 | Bjork et al. | |
| 4,239,747 A | 12/1980 | Pfeiffer et al. | |
| 4,406,878 A | 9/1983 | Deboer | |
| 4,439,356 A | 3/1984 | Khanna et al. | |
| 5,066,580 A | 11/1991 | Lee | |
| 5,198,136 A | 3/1993 | Tatemoto et al. | |
| 5,356,635 A * | 10/1994 | Raman ................. | A61K 9/2013 424/423 |
| 5,750,409 A | 5/1998 | Herrmann et al. | |
| 6,008,379 A | 12/1999 | Benson et al. | |
| 2001/0001038 A1 | 5/2001 | Matianich et al. | |
| 2005/0255045 A1 | 11/2005 | Woltering | |

FOREIGN PATENT DOCUMENTS

| | | |
|---|---|---|
| EP | 23992 A1 | 2/1981 |
| EP | 49745 A1 | 4/1982 |
| EP | 108638 A1 | 5/1984 |
| EP | 686046 A1 | 12/1995 |
| EP | 1006935 A1 | 6/2000 |
| EP | 1186305 A1 | 3/2002 |
| EP | 2098187 A1 | 9/2009 |
| WO | 9208691 A1 | 5/1992 |
| WO | 1997000240 A1 | 1/1997 |
| WO | 9966834 A1 | 12/1999 |
| WO | 0026179 A1 | 5/2000 |
| WO | 0115734 A2 | 3/2001 |
| WO | 03080554 A2 | 10/2003 |
| WO | 09071605 A1 | 6/2009 |
| WO | 2013076305 A1 | 5/2013 |
| WO | 2014187962 A1 | 11/2014 |
| WO | 2016079330 A1 | 5/2016 |
| WO | 2016079331 A1 | 5/2016 |
| WO | 2016079332 A1 | 5/2016 |

OTHER PUBLICATIONS

Hindenlang et al., "Iodine-containing radio-opaque polyphosphazenes", Polym. Chem., 1:1467-1474, Jun. 9, 2010.
Torchilin, V. "The Use of Plychelating and Amphiphilic Polymers in Gamma, MR and CT Imaging", Biomedical Polymers and Polymer Therapuetics, pp. 269-284 (2001).

* cited by examiner

*Primary Examiner* — Robert S Cabral
(74) *Attorney, Agent, or Firm* — Lando & Anastasi, LLP

(57) ABSTRACT

The present invention relates to a palpable marker composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 50,000 centipoise (cP) after administration, for use for identifying and/or locating a non palpable tumor. In one embodiment the composition the composition is a liquid before administration into the human or animal body that increases in viscosity by more than 500,000 centipoise (cP) after administration into the human or animal body. In another embodiment the composition is a liquid before administration and has the ability to transform into a crystalline or amorphous solid after administration.

23 Claims, 14 Drawing Sheets

PALPABLE MARKER COMPOSITION

CROSS-REFERENCE TO RELATED APPLICATIONS

This application is a U.S. national phase application and claims the benefit of priority under 35 U.S.C. § 371 of International (PCT) Patent Application Serial No. PCT/EP2017/062181, titled PALPABLE MARKER COMPOSITION and filed on May 19, 2017 which, in turn, claims priority to Swedish Patent Application Serial No. 1650695-8, filed on May 20, 2016.

FIELD OF THE INVENTION

The present invention provides a palpable marker composition for use to guide surgery of small non-palpable surgical targets.

TECHNICAL BACKGROUND

The interest for using biomaterials in biological systems is growing and have found wide interest for treatment of multiple diseases and conditions in humans and animals, such as pain, inflammation, infection, allergy and cancer. Advanced imaging techniques are furthermore important to diagnose patients and guide advanced treatments such as surgery and radiotherapy and new contrast markers and biomaterials to guide such procedures are of great importance. The present invention provides injectable liquids that gels or solidifies after administration to human or animal body after which it provides a system for acting as a tissue marker for guided surgery and/or imaging by one or multiple imaging modalities.

Every year more than 12 million people are diagnosed with cancer worldwide and over 7.5 million people die from cancer each year. These numbers are expected to increase because of population growth and due to the lifestyle in the Western world. There are four standard treatments of cancer; surgery, chemotherapy, radiotherapy and immunotherapy, which can be combined to provide treatment benefit for patients.

Lung cancer is the most common type of cancer across the globe. Global incidence of lung cancer was 1,608,055 in 2008 with the developing countries accounting for a major share (55%); 1,694,277 new cases were recorded in 2010 with U.S. Pat. Nos. 1,934,467, 2,213,561, and 2,530,820 as the predicted new cases for the years 2015, 2020, and 2025 respectively.

The current indication for Video Assisted Thoracic Surgery (VATS) procedures, as an example of a use for such product, is lung cancer of non-small cell lung cancer-type (NSCLC), which is one of the most commonly occurring cancers in the US and Europe, with >220,000 new cases of lung cancer in the US in 2015 and >380,000 cases in Europe in 2008.

The use of VATS procedures in the US is continuing to increase at approximately 5% per year from an estimated 26,000 per year in 2005 to 43,000 per year in 2014.

Stage I primary cancers are often too small to be palpated as well as early discovered metastases to the lung. An increasing use of early screening programs for lung tumors leads to the discovery of more and more very small lesions. Most such surgical targets are malignant lesions to be resected. In lung for example, this is small primary tumors or metastases below 5-10 mm in diameter. Larger lesions are often easier to locate by palpation and often require open surgery. There is hence a need for a marker that can be used in all clinical situations where the surgeon is often using palpation technique to identify a surgical target and where the target is too small to be identified.

SUMMARY OF THE INVENTION

The present invention relates to a palpable marker composition comprising non-water soluble carbohydrates and derivates thereof, wherein at least 50% of the non-water soluble carbohydrates are carbohydrates selected from derivatives of saccharides with at least one pyranose or furanose saccharide unit, such as derivatives of glucose og galactose, or derivatives of sucrose, lactose, maltose, trehalose, raffinose, glucosamine, galactosamine, lactosamine, or derivatives of disaccharides with at least one pyranose saccharide units or disaccharides with at least two pyranose saccharide units, trisaccharides, tetrasaccharides, or mixtures thereof, and wherein the composition is a liquid before administration into the human or animal body and increases in viscosity by more than 50,000 centipoise (cP) after administration, for use for identifying and/or locating a target tissue or becomes a semi-crystalline, crystalline or amorphous solid after administration for marking, identifying and/or locating a target tissue. In one embodiment the non-water soluble carbohydrates are selected from the group consisting of sucrose, lactose, maltose, trehalose, raffinose or derivatives of disaccharides with at least one pyranose unit. In one embodiment the palpable marker composition comprise non-water soluble carbohydrates, wherein at least 50% of the non-water soluble carbohydrates are carbohydrates selected from sucrose, lactose, maltose, trehalose, raffinose. In one embodiment the composition the composition is a liquid before administration into the human or animal body that increases in viscosity by more than 500,000 centipoise (cP) after administration into the human or animal body.

In another embodiment the composition is a liquid before administration and has the ability to transform into a gel-like material after administration.

In another embodiment the composition is a liquid before administration and precipitates into a solid after administration in human or animal body, wherein the solid can be a semi-crystalline, crystalline or amorphous solid.

In one embodiment an increase in viscosity or precipitation of a solid after administration into the human or animal body is due to diffusion of a molecule out of the administered material and into surrounding tissue.

In one embodiment is an increase in viscosity or precipitation into a solid after administration into the human or animal body is due to diffusion of solvent molecules out of the administered material and into surrounding tissue.

In one embodiment is the non-water soluble carbohydrates are disaccharides with structures selected from:

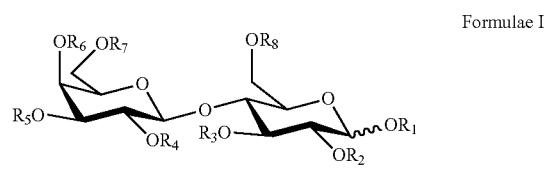

Formulae I

Formula II

Formula III wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting of acetyl, isobutyryl or propionyl;

and wherein both pure anomers and mixtures of α- and β-anomers of the above mentioned structural variations are claimed. In another embodiment the non-water soluble carbohydrates are trisaccharides with structures selected from:

Formulae IV

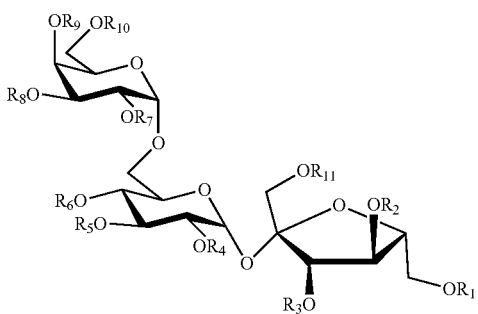

wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

In one embodiment at least 50% of the non-water soluble carbohydrates are mono- or oligosaccharides containing at least one amino sugar unit.

In one embodiment of the present invention, the amino sugar has the structure:

Formulae V wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, and mono-, di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of anomers such as α- and β-anomer centres of the above mentioned structural variations are claimed.

The present invention is implied to be compatible with various imaging modalities. In one embodiment the composition comprises contrast agents that makes the composition visible by PET imaging, SPECT imaging, Ultrasound imaging, x-ray imaging, fluorescence imaging, or optical coherence tomography (OCT) imaging. In one embodiment x-ray is selected from the group consisting of CT imaging and fluoroscopy imaging.

In another embodiment the composition comprises organic radioisotopes or inorganic radionuclides for use as internal radiotherapy such as brachytherapy or in imaging of tissue in humans or animals.

Various forms of administration are thinkable. In one embodiment the palpable marker composition is administered to the human or animal body through a syringe, an endoscope, a bronchoscope or a biopsy equipment to the target tissue preferably wherein the composition after insertion into the human or animal body becomes a semi-crystalline, crystalline or amorphous solid marker.

In one embodiment the present invention is a palpable marker composition that, once the palpable marker composition has been administered to the target tissue, the palpable marker composition is not moving. In one embodiment the present invention is a palpable marker composition for local administration, wherein at least 60% of an administrated amount of said palpable marker composition remains more than 24 hours within 10 cm from an injection point when the palpable marker composition is administrated to a human or animal body. In one embodiment preferably at least 50%, such as at least 55%, such as at least 60%, such as at least 65%, such as at least 70%, such as at least 75%, such as at least 80%, such as at least 85%, such as at least 90%, such as at least 95%, such as at least 99% of an administrated amount of said palpable marker composition remains more than 24 hours, such as more than 36 hours, such as more than 48 hours, such as more than 3 days, such as more than 4 days, such as more than 5 days, such as more than 6 days, such as at least one week, such as at least two weeks, such as at least three weeks, such as at least one month, such as at least six weeks, such as at least two months, such as at least three months, such as at least six months within at most 10 cm, such as within 8 cm, such as within 6 cm, such as within 5 cm, such as within 3 cm, such as within 2 cm, such as within 1 cm, such as within 0.5 cm, from an injection point when the palpable marker composition is administrated to a human or animal body. There are various forms of injection forms and routes possible, such as, but not limited to, transcutane injection, using a scope (bronchoscope, gastroscope, or any other flexible wired systems used to navigate inside a body), spraying or just adding on a open wound, attached to another such system, intracranial injection, inside air and fluent filled organs or cavities (e.g. bladder, stomach), or inside non naturally or medically created cavities.

Another aspect of the present invention relates to a method for identifying and/or locating a non-palpable tumor, a palpable tumor with higher accuracy and/or a target tissue by injection of a palpable marker composition, wherein the palpable marker composition is injected in soft tissue comprising inserting needle means into the soft tissue, identifying the position of said needle means in said soft tissue, further inserting said needle means into said soft tissue until one tip thereof reaches said non-palpable tumor, injecting palpable marker composition, wherein the palpable marker composition comprises non-water soluble carbohydrates, wherein at least 50% of the non-water soluble carbohydrates are carbohydrates selected from derivatives of monosaccharides, glucose, galactose, mannose, sucrose, lactose, maltose, trehalose, raffinose, glucosamine, galactosamine, lactosamine, or derivatives of disaccharides with at least one pyranose saccharide units or derivatives of disaccharides with at least two pyranose saccharide units, trisaccharides, tetrasaccharides, or mixtures thereof, and wherein the composition is a liquid before administration into the human or animal body and increases in viscosity by more than 50,000 centipoise (cP) after administration, or becomes a solid after administration, wherein the palpable marker composition is detectable by palpation.

In one embodiment the palpable marker composition stays substantially in the same position, for several days, preferably weeks once it has been administered into the soft tissue of a mammalian body.

In one embodiment the palpable marker composition is detectable by X-ray imaging, computed tomography (CT) imaging, magnetic resonance imaging (MRI), positron-emission tomography (PET) imaging, single photon emission computed tomography (SPECT) imaging, nuclear scintigraphy imaging, ultrasonography imaging, ultrasonic imaging, near-infrared imaging and/or fluorescence imaging.

In one embodiment the palpable marker composition is a liquid before administration into the human or animal body that increases in viscosity by more than 500,000 centipoise (cP) after administration into the human or animal body.

In one embodiment the palpable marker composition is a liquid before administration and has the ability to transform into a gel-like material after administration.

In one embodiment the palpable marker composition becomes a solid after administration, such as a semi-crystalline, crystalline or amorphous solid due to precipitation.

In one embodiment an increase in viscosity or precipitation of a solid of the palpable marker composition after administration into the human or animal body is due to diffusion of a molecule out of the administered material and into surrounding tissue.

In one embodiment an increase in viscosity or precipitation of a solid of the palpable marker composition after administration into the human or animal body is due to diffusion of solvent molecules out of the administered material and into surrounding tissue. In one embodiment the palpable marker composition stays within 10 cm from the site of injection, for several days, preferably weeks once it has been administered into the soft tissue of a mammalian or human body. In one embodiment the palpable marker composition is detectable by X-ray imaging, computed tomography (CT) imaging, magnetic resonance imaging (MRI), positron-emission tomography (PET) imaging, single photon emission computed tomography (SPECT) imaging, nuclear scintigraphy imaging, ultrasonography imaging, ultrasonic imaging, near-infrared imaging and/or fluorescence imaging. In one embodiment the palpable marker composition is a liquid before administration into the human or animal body that increases in viscosity by more than 10,000 centipoise (cP) after administration into the human or animal body.

In one embodiment the palpable marker composition is a liquid before administration and has the ability to transform into a gel-like material after administration due to diffusion of a molecule out of the administered material and into surrounding tissue. In one embodiment the palpable marker composition becomes a solid by precipitation after administration, such as a semi-crystalline, crystalline or amorphous solid due to diffusion of a molecule out of the administered material and into surrounding tissue. In one embodiment, an increase in viscosity or precipitation of the palpable marker composition after administration into the human or animal body is due to diffusion of solvent molecule out of the administered material and into surrounding tissue.

Another aspect of the present invention relates to use of a palpable marker composition according to the present invention, for identifying and/or locating a non-palpable tumor, or a palpable tumor with higher accuracy or security and/or a target tissue needed to be surgical removed or destroyed.

Yet another aspect of the present invention relates to a kit of parts for identifying and locating a non-palpable tumor, a palpable tumor with higher accuracy and/or a target tissue needed to be surgical removed or destroyed.

One embodiment comprises an injecting means suitable for being inserted into said soft tissue, allowing for administration of the palpable marker composition. Another embodiment comprises a needle means comprising a hollow cylindrical body and a releasable fixed tip to one end of said cylindrical body, the fixed tip further comprise fixing means for fixing into said soft tissue.

In one embodiment said tip is provided with a shank insertable into a cavity of said body, said shank is further provided with a longitudinal through cavity.

In one embodiment the tip comprises an internal cavity, the internal cavity adapted for communication with the longitudinal through cavity of the shank.

In one embodiment tip comprise holes, adapted for communication with the internal cavity of the tip. But any other standard equipment needed to take biopsy with or to inject any fluent into the body can generally be used.

DETAILED DESCRIPTION OF THE INVENTION

Figure 1:
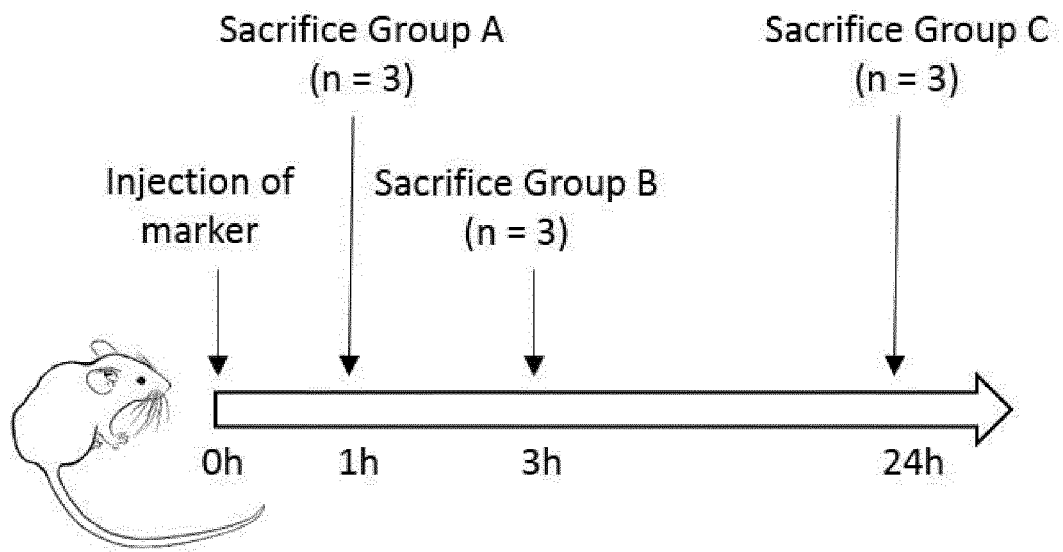
FIG. 1. Schedule for animal dosing and sacrifice.

The present invention discloses a palpable marker composition comprising non-water soluble carbohydrates, wherein at least 50% of the non-water soluble carbohydrates are carbohydrates selected from derivatives of monosaccharides, glucose, galactose, mannose, sucrose, lactose, maltose, trehalose, raffinose, glucosamine, galactosamine, lactosamine, or derivatives of disaccharides with at least one pyranose saccharide units or derivatives of disaccharides with at least two pyranose saccharide units, trisaccharides, tetrasaccharides, or mixtures thereof, and wherein the composition is a liquid before administration into the human or animal body and increases in viscosity by more than 50,000 centipoise (cP) after administration, or becomes a solid after administration, wherein the palpable marker composition is detectable by palpation, for use for identifying and/or locating a non palpable tumor.

Definitions

"Non-water soluble carbohydrates" refers to carbohydrates that have low solubility in water, which is defined as carbohydrates that precipitates when the concentration exceeds 0.025 M at 25 degrees Celsius.

The term "gel" as used in the present invention includes systems such as gels, which upon injection into a human or an animal increases viscosity where the composition changes from being liquid like to gel like in its appearance.

The term "precipitation" or "precipitates" as used in the present invention includes formation of a solid after injection of a liquid composition into soft tissue, wherein the solid can be a semi-crystalline, crystalline or amorphous solid In the context of the present invention, a "marker" or "tissue marker" is a detectable agent or composition which does not move, or stays substantially in the same position, said remains within 10 cm of the site of injection, for several days or weeks once it has been administered or implanted into a specific site or tissue of a mammalian body. A tissue marker can, for example, comprise one or more X-ray contrast agents, radioactive compounds, paramagnetic compounds, fluorescent agents, ultrasound contrast agent, agents visible with PET imaging, or other detectable agents.

An "imagable tissue marker" or "imagable marker" comprises a detectable agent in a form and/or a sufficient amount to allow for detection of the tissue marker by an external imaging modality if administered or implanted into a mammalian body. Exemplary external imaging modalities include, but are not limited to, X-ray imaging, such as CT imaging, MRI, PET imaging, single photon emission computed tomography (SPECT) imaging, nuclear scintigraphy imaging, ultrasonography imaging, ultrasonic imaging, near-infrared imaging and/or fluorescence imaging.

With the term "carbohydrates", as used herein, we refer to monosaccharides, disaccharides and trisaccharides or oligosaccharides, including amino sugars.

With the term "hydrofobicity" we refer to the effect that molecule is seemingly repelled from water, which means that it has a very low solubility in water.

With the term "viscosity" we refer to that the viscosity of a fluid is a measure of its resistance to gradual deformation by shear stress or tensile stress With the term "gel" compound or material, as used herein, we refer to any compound comprising some of the properties of a gel i.e. a material that exhibits limited flow when in the steady-state.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable.

The term "palliation", and variations thereof, as used herein, means that the extent and/or undesirable manifestations of a physiological condition or symptom are lessened and/or time course of the progression is slowed or lengthened, as compared to not administering compositions of the present invention.

Palpable means that it can be felt using physical examination with fingers with a good predictability, accuracy and reproducibility.

The formulation is preferably in the form adapted for parenteral administration and/or for administration using topical route, and/or for administration using intracavitary routes such as bladder, uterus, and vagina, and should preferably consist of pharmaceutically acceptable constituents. The formulation that as such has a comparable low viscosity is intended for injection in the body of a human or animal, where after the formulation becomes more viscous or becomes a solid. It is preferred that the viscosity of the formulation after injection in the body of a human or animal increases by at least 50%, such as at least 80%, such as at least 100%, or at least 150%, or at least 200%, or at least 300%, or at least 500%, or at least 750%, or at least 1000%, or at least 10,000%, or that the formulation becomes essentially solid (non-viscous).

The formulation is preferably adapted for injection via a thin needle used for injection into a body or surgical related procedures, such as but not limited to biopsy. The viscosity of the gel-forming formulation before injection can be any suitable viscosity such that the formulation can be parenterally administered to a patient.

Exemplary formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 20° C.

Alternative formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 5° C. When referred to herein, the (dynamic) viscosity is measured at the specified temperature in accordance with the method described in ASTM D7483. Gels in the present invention are formed by hydrophobic interactions and/or physical (non-covalent) cross-links by complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment. Chemical (covalent) cross linking may be accomplished by any of a number of mechanisms, including free radical polymerization, condensation polymerization, anionic or cationic polymerization, step growth polymerization, electrophile-nucleophile reactions, combinations thereof, and the like.

The gel or solid forming compositions may be loaded with organic x-ray agents such as iodinated polymers or sugars and nanoparticles or submicron particles either prior to or during gel formation, such as when the gel is in a liquid state or in transition to the gel-state, e.g., by diffusion into the gel composition. These x-ray agents or particles may either be entrapped in the hydrogel matrix without any chemical bond, or they may be bonded, non-covalently or covalently, to the gel composition. The organic x-ray agents may be one component in the gel and the particles another component, where the particles are either a contrast agent for imaging by x-ray, MRI, PET, SPECT, fluorescence, proton radiation or ultrasound including HIFU, and/or contain pharmaceutical agents. Pharmaceutical agents may be, but not limited to, radiosensitzers, chemotherapeutics, immunomodulators, anesthetics or hormones. MRI agents such as gadolinium may be a component in the gel forming systems. Pharmaceutical agents can furthermore be covalent or non-covalently embedded in the gel. After injection, the gelled or solidified formulation typically provides a well defined marker that remains at the injection site for several days, weeks or months and may contain an assembly of imaging contrast agents which provides contrast in e.g. X-ray imaging, and which may serve as a tissue marker, thus, enabling tracking of tissue or tumor movement during e.g. radiotherapy or surgical procedures.

The gel or solid forming system may be used for aid or guidance of one or more external or internal stimuli (or a combination of both). It may also be used in combination with external or internal stimuli to enhance the therapeutic effect of the stimuli. In one interesting embodiment, the gel forming system may be used in combination with photodynamic therapy (PDT) in combination with a drug (photosensitizer or photosensitizing agent) with a specific type of light to kill cancer cells. In another embodiment, the gel forming system may be used in combination with hyperthermia based treatments such as high-intensity focused ultrasound (HIFU), radiofrequency thermal ablation (RFA) and laser-induced interstitial thermotherapy (LITT), but not limited to those. In high-intensity focused ultrasound (HIFU) the gel forming system may be used to direct or aid in delivery of acoustic energy into the desired tissue thereby destroying the diseased tissue by e.g. thermal ablation (coagulation necrosis). In another embodiment, the gel forming system may be used to direct or aid in insertion of the needle electrode into the target site for use in radiofrequency thermal ablation (RFA). In yet another embodiment, the gel forming system may be used to direct or aid in Laser-induced interstitial thermotherapy (LITT) to ensure correct laser irradiation of the target tissue.

Gel or Solid Forming Component

Suitable gel-forming components include those composed of organic constituents such as derivatized saccharides such as esterified saccharides, derivatized polyols such as esterified polyols, polymers, lipids, peptides, proteins, low molecular weight gelators and non-water soluble high-viscosity liquid carrier materials as well as combinations hereof.

In one specific embodiment of the invention the hydration sensitive gel or solid forming component is hydrophobic saccharides. Preferred scaffolds are monosaccharides, disaccharides, trisaccharides, or oligosaccharides. Other suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units. Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate or activation reagents such as N-(3-Dimethylaminopropyl)-N'-ethylcarbodiimide (EDC), N,N'-Dicyclohexylcarbodiimide (DCC), O-(7-azabenzotriazol-1-yl)-N,N,N',N'-tetramethyluronium hexafluorophosphate (HATU) and the like can be used.

The acyl groups forming the acyloxy substituents of the invention may be any moiety derived from a carboxylic acid. More particularly, the acyl groups of the compositions of the invention may be of the RCO—, where R is optionally oxy-substituted alkyl of 2-10 carbon atoms which may be linear or branched hydrocarbons with one or more functional groups present in the chain. Using carboxylic acids and/or polyols of different chain length and using carboxylic acids having oxy-substitution allows control of the degree of hydrophilicity and of the solubility of the resulting ester. Such materials are sufficiently resistant to dissolution in vivo that they are able to form stabile hydrophobic gels, which may encapsulate the active pharmaceutical ingredients and/or the contrast agents of the present invention.

Suitable monosaccharides in either D or L-form include but are not limited to the following structures, in which α,β anomeric mixtures at any ratio may exist: Glucosamine, Galactosamine, Mannosamine, Mannose, Rhamnose, Rhamnosamine, Galactose, Allose, Allosamine, Altrose, Altrosamine, Gulose, Gulosamine, Idose, Idosamine, Talose and Talosamine.

Suitable disaccharides, include but are not limited to the following structures in which α,β0 anomeric mixtures at any ratio may exist, and where the individual sugars may be linked by either α or β glycosidic bonds and the individual sugars can D or L: Galp-(1→2)-Glc, Galp-(1→3)-GlcN, Galp-(1→4)-Glc, Glcp-(1→4)-Glc, Glcp-(1→6)-Glc, Glcp-(1→2)-GlcN, Galp-(1→4)-ManN, Glcp-(1→4)-GalN, Manp-(1→3)-Glc, ManNp-(1→4)-Gal, GalNp-(1→3)-ManN, GlcNp-(1→6)-GalN, Rhamnp-(1→6)-Glc, Glcp-(1↔1)-Glcp, Talp-(1→4)-Glu, Glup (1→3)-Ido, GlcAlp-(1→4)-GlcN, GlcAlp-(1→6)-GlcN.

Suitable trisaccharides include but are not limited to the following structures in which α,β0 anomeric mixtures at any ratio may exist, and where the individual sugars can be linked by either α or β glycosidic bonds and the individual sugars can be D or L: Galp-(1→2)-Glcp-(1→3)-Galp, Galp-(1→4)-Glcp-(1→6)-GlcN, Galp-(1→4)-Glcp-(1→6)-Gal, Glcp-(1→4)-Glcp-(1→4)-Glcp Glcp-(1→6)-Glcp-(1→6)-Glc, Galp-(1→6)-Glcp (1↔2)-Fruf, Glcp-(1→3)-Fruf-(2↔1)-Glcp, Galp-(1→4)-ManNp-(1→3)-Glu, Glcp-(1→4)-GalN-(1→2)-Man, Manp-(1→3)-Glcp-(1→4)-GlcN, ManNp-(1→4)-Galp-(1→3)-Glc, GalNp-(1→3)-ManNp-(1→6)-GlcN. Rhamnp-(1→6)-Glcp Galp-(1→6)-Glcp-(1↔1)-Glcp, Talp-(1→4)-Glup-(1→2)-Man, Glup (1→3)-Idop-(1→6)-Glu, GlcAlp-(1→6)-GlcAlp (1→4)-GlcN.

Suitable tetrasaccharides include but are not limited to the following structures in which α,β anomeric mixtures at any ratio may exist, and where the individual sugars can be linked by either α or β glycosidic bonds and the individual sugars can be D or L: Galp-(1→4)-Glcp-(1→6)-glcp-(1→4)-Glc, Galp-(1→4)-Glcp-(1→4)-Glcp-(1→4)-Glcp-(1→4)-Glc, Galp-(1→4)-Glcp-(1→4)-Galp-(1→4)-Glc, Glcp-(1→4)-Glcp-(1→4)-Glcp-(1→4)-Glc, Galp-(1→6)-Glcp-(1→6)-Galp-(1→6)-Glc, Galp-(1→6)-Glcp-(1→6)-Galp-(1→4)-Glc, Galp-(1→6)-Glcp-(1→6)-Glcp-(1→4)-Glc, GlcNp-(1→4)-GlcNp-(1→6)-GlcNp-(1→4)-GlcN, GlcNp-(1→6)-Galp-(1→6)-Glcp-(1↔2)-Fruf, Galp-(1→4)-Glcp-(1→3)-Fruf-(2↔1)-Glcp, Talp-(1→4)-Glup-(1→2)-Man-(1-3)-Glu, Glup (1→3)-Idop-(1→6)-Glup-(1→2)-Gal.

Solvent

The composition of the solvent (dispersion medium) should not be particularly limited, and examples include biocompatible organic solvents such as ethanol, ethyl lactate, propylene carbonate, glycofurol, N-methylpyrrolidone, 2-pyrrolidone, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, such as but not limited to N-methyl-2-pyrrolidone, glycofurol, polyethylene glycol (PEG), benzyl benzoate, triglycerides, acetone, benzyl alcohol, N-(betahydromethyl) lactamide, butylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, esters of caprylic and/or capric acids with glycerol or alkylene glycols, oleic acid, peanut oil, polyethylene glycol, propylene carbonate, 2-pyrrolidone, sesame oil, [±]-2,2-dimethyl-1,3-dioxolane-4-methanol, tetrahydrofuran, diethylene glycol monoethyl ether, carbitol, triacetin, triethyl citrate, and combinations thereof; or desirably from trichlorofluoromethane, dichlorofluoromethane, tetrafluoroethane (R-134a), dimethyl ether, propane, butane, and combinations thereof; or specifically from caprylic/capric triglyceride, oleic acid, 1-dodecylazacycloheptan-2-one and the like. Although the formulation can be stably dispersed in these solvents (dispersion media), the solvents may be further added with a saccharide derivatives of for example, triglycerides such as tri-pentanoyl glycerol, tri-octanoyl glycerol, tri-dodecanoyl glycerol, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as α-, β-, or γ-cyclodextrin, sugar alcohol such as erythritol, xylitol, sorbitol, mannitol, and maltitol, or a polyhydric alcohol such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol. Additives may furthermore be selected from the group consisting of bio-available materials such as amiloride, procainamide, acetyl-beta-methylcholine, spermine, spermidine, lysozyme, fibroin, albumin, collagen, transforming growth factor-beta (TGF-beta), bone morphogenetic proteins (BMPs), fibroblast growth factor (bFGF), dexamethason, vascular endothelial growth factor (VEGF), fibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl, isopropyl myristate, Eudragit, tego betain, dimyristoylphosphatidylcholine, scleroglucan, and the like; organic solvents such as cremophor EL, ethanol, dimethyl sulfoxide, and the like; preservatives such as methylparaben and the like; sugars such as starch and derivatives thereof, sugar-containing polyols such as sucrose-mannitol, glucose-mannitol, and the like; amino acids such as alanine, arginine, glycine, and the like; polymer-containing polyols such as trehalose-PEG; sucrose-PEG, sucrose-dextran, and the like; sugar-containing amino acid such as sorbitol-glycine, sucrose-glycine, and the like; surfactants such as poloxamer of various molecular weights, Tween 20 Tween 80, Triton X-100, sodium dodecyl sulfate (SDS), Brij, and the like; sugar-containing ions such as trehalose-$ZnSO_4$, maltose-$ZnSO_4$, and the like; and bio-acceptable salts such as silicate, NaCl, KCl, NaBr, NaI, LiCl, n-$Bu_4NBr$, n-$Pr_4NBr$, $Et_4NBr$, $Mg(OH)_2$, $Ca(OH)_2$, $ZnCO_3$, $Ca_3(PO_4)_2$, $ZnCl_2$, $(C_2H_3O_2)_2Zn$, $ZnCO_3$, $CdCl_2$, $HgCl_2$, CaCl2), $(CaNO_3)_2$, $BaCl_2$, $MgCl_2$, $PbCl_2$, $AlCl_2$, $FeCl_3$, $NiCl_2$, $AgCl$, $AuCl$, $CuCl_2$, sodium tetradecyl sulfate, dodecyltrimethylammonium bromide, dodecyltrimethylammonium chloride, tetradecyltrimethyl-ammonium bromide, and the like, but not limited to those.

In one embodiment of the present invention, the content of the additive is from $1\times10^{-6}$-50 wt %, preferably $1\times10^{-3}$ to 30 wt %, based on the total weight of the gel forming component(s).

Contrast Agents

Contrast may be achieved using organic x-ray contrast agents, such as radiopaque agents such as iodinated compounds, which may be combined with chelators of MRI agents such as gadolinium, and/or combined with chelators of PET imaging agents such as copper-64, which may further be combined with solid inorganic particles. Chelators may be DOTA, EDTA, or DTPA and chelators will be non-covalently embedded or covalently conjugated to the gel-forming components. The combined contrast agents should preferably be visible by at least x-ray imaging. In one embodiment the combined contrast agents is visible by CT. Preferred contrast agents are iodinated compounds such as polymers or sugar molecules such as derivatives of glucose or sucrose or other oligosaccharides. Solid particles may comprise, or consist of, one or more X-ray contrast agents, i.e., compounds that are able to block or attenuate X-ray radiation. Such compounds include transition metals, rare earth metals, alkali metals, alkali earth metals, other metals, as defined by the periodic table. A metal or alkali metal may appear in non-oxidized or any of the existing oxidation states for the metal. These oxidation states include monovalent cations, divalent cations, trivalent cations, tetravalent cations, pentavalent cations, hexavalent cations and heptavalent cations.

In one embodiment, the one or more X-ray contrast agents are selected from iodine (I), gold (Au), bismuth (Bi), gadolinium (Gd), iron (Fe), barium (Ba), calcium (Ca) and magnesium (Mg). In a particular embodiment, the detectable compound comprises one or more compounds selected from the group of gold (Au) and bismuth (Bi). The one or more X-ray contrast agents are typically present in metal form, in alloy form, in oxide form or in salt form. It should be understood that besides iodinated compounds which provides a useful contrast for X-ray imaging, the formulation may also include solid particles that are visible by X-ray imaging or other imaging modalities than X-ray imaging. In one embodiment, the solid-particles are furthermore visible by MR and/or PET imaging, or by other imaging modalities.

In a particular embodiment, the gel-forming composition may further comprise a radioactive or paramagnetic compound for one or more imaging modalities such as MRI, PET imaging, SPECT imaging, nuclear scintigraphy imaging, ultrasonography imaging, ultrasonic imaging, near-infrared imaging and/or fluorescence imaging.

In some interesting embodiments, the formulation according to any one of the preceding claims, contain solid particles that comprise one or more radioactive, paramagnetic or ferromagnetic particles.

Moreover, individual particles may comprise two or more types of compounds which are visible in different imaging modalities.

Said radioactive compounds may comprise isotopes of Copper ($^{61}Cu$, $^{64}Cu$, and $^{67}Cu$), Iodide ($^{123}I$, $^{124}I$, $^{125}I$, $^{131}I$), Indium ($^{111}In$), Technetium ($^{99m}Tc$), Rhenium ($^{186}Re$, $^{188}Re$), Gallium ($^{67}Ga$, $^{68}Ga$), Strontium ($^{89}Sr$), Samarium ($^{153}Sm$), Ytterbium ($^{169}Yb$), Thallium, ($^{201}Tl$), Astatine ($^{211}At$), Lutetium ($^{177}Lu$), Actinium ($^{225}Ac$), Yttrium ($^{90}Y$), Antimony ($^{119}Sb$), Tin ($^{117}Sn$, $^{113}Sn$), Dysprosium ($^{159}Dy$), Cobalt ($^{56}Co$), Iron ($^{59}Fe$), Ruthenium ($^{97}Ru$, $^{103}Ru$), Palladium ($^{103}Pd$), Cadmium ($^{115}Cd$), Tellurium ($^{118}Te$, $^{123}Te$), Barium ($^{131}Ba$, $^{140}Ba$), Gadolinium ($^{149}Gd$, $^{151}Gd$), Terbium, ($^{160}Tb$), Gold ($^{198}Au$, $^{199}Au$), Lanthanum ($^{140}La$), Zirconium ($^{89}Zr$), Titanium ($^{45}Ti$) and Radium ($^{223}Ra$, $^{224}Ra$), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Said paramagnetic or ferromagnetic compounds may also be selected from the group of Scandium (Sc), Yttrium (Y), Lanthanum (La), Titanium (Ti), Zirconium (Zr), Hafnium (Hf), Vandium (V), Niobium (Nb), Tantalum (Ta); Chromium (Cr), Molybdenium (Mo), Tungsten (W), Manganese (Mn), Technetium (Tc), Rhenium (Re), Iron (Fe), Ruthenium (Ru), Osmium (Os), Cobalt (Co), Rhodium (Rh), Iridium (Ir), Nickel (Ni), Palladium (Pd), Platinum (Pt), Copper (Cu), Silver (Ag), Gold (Au), Zinc (Zn), Cadmium (Cd), Mercury (Hg), the lanthanides such as Lathanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu)) and the actinides such as Actinium (Ac), Thorium (Th), Protactinium (Pa), Uranium (U), Neptunium (Np), Plutonium (Pu), Americium (Am), Curium (Cm), Berkelium (Bk), Californium (Cf), Einsteinium (Es), Fermium (Fm), Mendelevium (Md), Nobelium (No) and Lawrencium (Lr), wherein said paramagnetic or ferromagnetic compounds may appear in any of the existing oxidation states for the metal. These oxidation states include monovalent cations, divalent cations, trivalent cations, tetravalent cations, pentavalent cations, hexavalent cations and heptavalent cations.

Said one or more radioactive, paramagnetic or ferromagnetic compounds may be covalently linked to gel-forming components or the nano-sized particles or non-covalently associated with the gel-forming components or nano-sized particles.

In one embodiment, the gel-forming components or nano-sized particles further comprise one or more fluorophore compounds for near infrared fluorescence imaging. Said compounds may comprise a fluorescent proteins, peptides, or fluorescent dye molecules. Common classes of fluorescent dyes include xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Typical fluorescein dyes include 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356.

The species may also include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED), and other rhodamine dyes. The species may alternatively include a cyanine dye, such as, for example, Cy3, Cy3B, Cy3.5, Cy5, Cy5.5, Cy. Or IRDye 800CW, IRDye 680LT, Qdot 800 nanocrystal, Qdot 705 nanocrystal or porphyrazine compounds In another embodiment, the nano-sized particles further comprise or consist of one or more gasses encapsulated in lipid, polymer or inorganic based particles for ultrasonography imaging. Said gasses may comprise air, sulphur halides such as sulphur hexafluoride or disulphur decafluoride; fluorocarbons such as perfluorocarbons; fluorinated (e.g. perfluorinated) ketones such as perfluoroacetone; and fluorinated (e.g. perfluorinated) ethers such as perfluorodiethyl ether. Representative perfluorocarbons, which may for example contain up to 7 carbon atoms, include perfluoroalkanes such as perfluoromethane, perfluoroethane, perfluoropropanes, perfluorobutanes (e.g. perfluoro-n-butane, optionally in a mixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane; and mixtures of any of the foregoing, including mixtures with gases such as nitrogen, carbon dioxide, oxygen etc, but not limited to those.

In another embodiment, x-ray contrast in achieved using small organic iodine containing compounds. Said small organic iodine containing compounds includes commercial available iodinated contrast agents such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™) iomeprol (marketed e.g. under the trade name Iomeron™) and the non-ionic dimer iodixanol (marketed under the trade name and Visipaque™). Additional examples of small organic iodine containing compounds includes the ones disclosed in WO2009/071605, EP1186305, EP686046, EP108638, EP0049745, EP0023992, WO2003080554, WO2000026179, WO1997000240, WO9208691, U.S. Pat. Nos. 3,804,892, 4,239,747, 3,763,226, 3,763,227 and 3,678, 152, but not limited to those. In another interesting embodiment, the said small organic iodine containing compounds includes iodinated derivates of sucrose acetate isobutyrate (SAIB). In contrast to what is disclosed in for example EP1006935, where a composition for controlled release of a substance is disclosed which composition comprises SAIB, this specific embodiment according to the present invention aims at providing a stable contrast agent embedded in such matrixes. Such compounds may be used alone or in combination with solid particles to achieve an injectable gel visible by at least CT imaging. In one specific embodiment of the invention the hydration sensitive gel forming component is sucrose acetate isobutyrate (SAIB) a hydrophobic component composed of sucrose (the scaffold), which has been acylated with isobutyrate and acetate. Preferred scaffolds of this invention are monosaccharides, disaccharides or trisaccharides. A particularly preferred disacharide scaffold are sucrose and lactose, however, the alcohol containing scaffold may be derived from a polyhydroxy alcohol having from about 2 to about 20 hydroxy groups and may be formed by esterifying 1 to 20 polyol molecules. Suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units.

Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate or activation reagents such as N-(3-Dimethylaminopropyl)-N'-ethylcarbodiimide (EDC), N,N'-Dicyclohexylcarbodiimide (DCC), O-(7-azabenzotriazol-1-yl)-N,N,N',N'-tetramethyluronium hexafluorophosphate (HATU) and the like can be used.

The acyl groups forming the acyloxy substituents of the invention may be any moiety derived from a carboxylic acid. More particularly, the acyl groups of the compositions of the invention may be of the RCO—, where R is optionally oxy-substituted alkyl of 2-10 carbon atoms which may be linear or branched hydrocarbons with one or more functional groups present in the chain. Using carboxylic acids and/or polyols of different chain length and using carboxylic acids having oxy-substitution allows control of the degree of hydrophilicity and of the solubility of the resulting ester. Such materials are sufficiently resistant to dissolution in vivo that they are able to form stabile hydrophobic gels which may encapsulate the said contrast agents of the present invention.

In one embodiment the composition for use is a palpable marker composition comprising one or more iodinated polymers, iodinated oligomers, iodinated lipids, iodinated saccharides, iodinated disaccharides, iodinated polysaccharides, iodinated peptides, or a derivative or a combination thereof. The composition for use according to the present invention, wherein the composition comprises iodinated derivates of carbohydrate or iodinated derivative of polyalcohols, such as iodinated derivatives of sucrose acetate isobutyrate (SAIB), such as iodinated derivatives of lactose, such as iodinated derivatives of trehalose, such as iodinated derivatives of arabinose, such as iodinated derivatives of maltose, such as iodinated derivatives of glucose, such as iodinated derivatives of galactose, iodinated derivatives of glucosamine, such as iodinated glucosamine, and the like. In yet another embodiment the composition comprises an iodinated derivate of a carbohydrate doped into a composition of the same class of non-idoninated carbohydrate derivatives.

Further, in one embodiment, the palpable marker composition comprises sucrose acetate isobutyrate (SAIB) or a derivative thereof and in one specific embodiment of the present invention, the palpable marker composition comprises an iodinated derivate of sucrose acetate isobutyrate (SAIB). Furthermore in another specific embodiment of the present invention the palpable marker composition comprises an iodinated derivate of sucrose acetate isobutyrate (SAIB) doped into sucrose acetate isobutyrate (SAIB). This has been evaluated for stability and the amount of this iodo-SAIB/SAIB that can be doped into SAIB, is at least 50 mol %.

The iodo-SAIB provides high X-ray contrast. The iodo-SAIB compound is poorly soluble in ethanol and is a white amorphous solid whereas SAIB is highly soluble in ethanol and is a highly viscous liquid. However, a mixture of ethanol and SAIB can solubilize iodo-SAIB. This means that the SAIB helps solubility of iodo-SAIB, which is an interesting feature and which provides an injectable solution which gelates after administration (through a thin needle, thinner than 20 gauge) that can function as a high contrast X-ray marker.

When injected into mice, the iodo-SAIB/SAIB provides high contrast and has the desirable stability properties. Furthermore, the gel seems homogeneous.

In one embodiment of the present invention the palpable marker composition comprises an iodinated derivate of sucrose acetate isobutyrate (SAIB) solubilised in a mixture of ethanol and sucrose acetate isobutyrate (SAIB).

Features of injectable medical gel-forming system (1) In order to be injectable, the system should be in a sol state such as a liquid like state before administration. The sol state should be of sufficiently low viscosity—typically lower than 10,000 cP, preferably lower than 2,000 cP, at 20° C. (or alternatively lower than lower than 10,000 cP, preferably 2,000 cP, at 5° C.)—to allow for small needle head to alleviate the patient discomfort and simplify insertion procedure.

(2) Gelation via physical association or hydration starts to happen or is complete after injection.

(3) The gels or solids should be biodegradable or gradually dissolvable within a controlled time period, and the products should be cleared/secreted through normal pathways.

(4) The polymer itself and the degradable products should be biocompatible. Likewise, if additives are added, such as cross-linking agents, initiators etc. these should also be biocompatible.

(5) The gel could potentially have cell/tissue-adhesive properties.

It should be understood, that the gel-forming system should preferably be biocompatible, i.e. does not stimulate a severe, long-lived or escalating biological response to the formulation when injected into a mammal, in particular a human. To facilitate metabolism of the gel scaffold, degradable linkages can be included through the use of polylactide, polyglycolide, poly(lactide-co-glycolide), polyphosphazine, polyphosphate, polycarbonate, polyamino acid, polyanhydride, and polyorthoester-based building blocks, among others. Additionally, small molecule crosslinking agents containing similar hydrolyzable moieties as the polymers such as carbonates, esters, urethanes, orthoesters, amides, imides, imidoxy, hydrazides, thiocarbazides, and phosphates may be used as building blocks. Additionally, polyglycolide diacrylate, polyorthoester diacrylate and acrylate-substituted polyphosphazine, acrylate-substituted polyamino acid, or acrylate-substituted polyphosphate polymers can be used as degradable building blocks. Methacrylate or acrylamide moieties can be employed instead of acrylate moieties in the above examples. Similarly, small molecules containing a hydrolyzable segment and two or more acrylates, methacrylates, or acrylamides may be used. Such degradable polymers and small molecule building blocks may be functionalized with acrylate, methacrylate, acrylamide or similar moieties by methods known in the art.

In order to be injectability, the system should be in a sol state before administration. The sol state should be of sufficiently low viscosity to allow for small needle head to alleviate the patient discomfort and simplify insertion procedure. Gelation or precipitation via physical association starts to happen or is complete after injection.

In one embodiment, the composition according to the present invention is administered using topical route.

In one embodiment, the composition according to the present invention is intra-cavitary administration into existing or established body cavities. The existing cavities include, but are not limited to; urinary bladder, uterus, gall bladder, sinuses, middle ear. The established or formed cavities include, but are not limited to cavities formed in relation to surgery and infections.

Viscosity of the Formulation

The viscosity of the formulation is before the injection preferably lower than 10,000 cP, in particular lower than 2,000 cP, at 20° C.

Alternatively, the viscosity of the formulation is before the injection typically lower than 2,000 cP at 5° C.

In one embodiment, the gel-forming system of the formulation is preferably one which, after injection or under conditions mimicking those in a human body, forms a gel having a viscosity at 37° C. in the range of 50,000 to 500,000,000,000 cP. More particularly, the viscosity of the gel can be about 50,000 cP, about 75,000 cP, about 100,000 cP, about 125,000 cP, about 150,000 cP, about 200,000 cP, about 30,000 cP, about 800,000 cP, about 1,000,000 cP, about 2,000,000 cP, about 5,000,000 cP, about 10,000,000 cP, about 20,000,000 cP, about 30,000,000 cP, about 40,000,000 cP, about 50,000,000 cP, about 500,000,000,000, or ranges thereof. Preferably, the viscosity of the gel after injection (i.e. when present in the desired location) is above 50,000 cP, e.g. in the range of 50,000 cP to 1,000,000,000 cP. In particular, the formulation after injection is preferably essentially solid.

Preferred Properties of the Gel-Forming or Solid-Forming System

In one embodiment, the preferred systems include non-water soluble high-viscosity or solid materials such as non-water soluble carbohydrates and in particular carbohydrates selected from derivatives of monosaccharides, disaccharides with at least two pyranose saccharide units, trisaccharides, tetrasaccharides or mixtures thereof, or derivatives of lactose, maltose, trehalose, raffinose, glucosamine, galactosamine, lactosamine, or mixtures thereof. Such systems may be mixed with solid particles that carry drug or contrast agent followed by parental injection, thus functioning as a injectable composition, which that can be visualized by one or multiple imaging modalities, including X-ray imaging.

In one embodiment of the invention the composition comprising a non-water soluble carbohydrate, wherein the composition is a liquid before administration into the human or animal body and increases in viscosity by more than 50,000 centipoise (cP) after administration. In one embodiment of the invention the composition comprising a non-water soluble carbohydrate, wherein the composition is a liquid before administration into the human or animal body and increases in viscosity by more than 500,000 centipoise (cP) after administration.

In one embodiment, at least 60% of an administrated amount of the non-water soluble carbohydrate remains more than 24 hours within 10 cm from an injection point when administrated to a human or animal body.

Other Constituents of the Formulation

In one embodiment a polymer may be used to work as a stabilizer between gel and biological surrounding and therefore, the composition may also comprise a molecule that increase gel or solid stability in the human or animal body, such as an amphiphilic molecule, such as an emulsifier. Therefore in one embodiment the composition comprises poly(ethylene glycol-b-caprolactone) (PEG-PCL), sucrose acetate isobutyrate (SAIB), poly(D,L-lactic acid) (PLA), or poly(lactic-co-glycolic acid) (PGLA), or a combination thereof. The formulation may further comprise compounds or polymers, which are visible in imaging modalities other than X-ray imaging.

In one embodiment, the formulation further comprises an iodine-containing polymer, e.g. polyvinylpyrrolidone-iodine (PVP-I), or one selected from i) Polym. Chem., 2010, 1, 1467-1474, ii) U.S. Pat. No. 3,852,341, iii) U.S. Pat. No. 4,406,878, iv) U.S. Pat. No. 5,198,136, v) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein. Such polymers can be added to the gel forming components prior to gelation and function as contrast agent in vivo. Such polymers may additionally or alternatively be covalently bound to the one or more of the gel forming components or adhered to the particles of the present invention.

In one specific embodiment, the formulation consist of iodinated SAIB as contrast agent with high HU-contrast or an iodinated carbohydrate derivate. Cancer surgery can basically be divided in two categories: open surgery and minimal invasive surgery (MIS). MIS is becoming standard of care when resecting smaller lesions at locations that are accessible with a MIS approach. All target locations that can be reached by the surgeon's index finger (superficial parts of the body) can benefit from using the present invention when resecting smaller lesions. MIS approached is often performed video assisted such as for example video assisted thoracic surgery (VATS).

The present invention as surgical palpation technique may be used in combination with MIS of lung, liver, pancreas and thymus.

The present invention, a palpable marker composition, is in one embodiment a marker with the intended use to guide surgery of small non-palpable surgical targets. One key feature of the product is implied to be that the surgeon can: 1) Easily place it (liquid at placement) using their advance scope equipment; 2) Feel it (change into hard solid material) through tissue during surgery using the index finger. The present invention is moreover visible on commonly used medical imaging modalities such as X-ray, MRI and Ultrasound making it possible to identify the marker throughout the clinical workflow.

The present invention may be provided as a sterile liquid in ampoules containing 1 mL each. In one embodiment the palpable marker composition is colored. In one embodiment the palpable marker composition is blue. It has initially a low initial viscosity (liquid). In one embodiment, once injected into soft tissue, the present invention turn into a hard crystalline or amorphous solid marker or a highly viscous gel.

The liquid feature of the marker makes it possible inject with thin needles and thereby enabling injection via bronchoscopes and endoscopes. Peripheral parts of the body in e.g. the lung can thus be reached with minimal risk of causing a trauma (pneumothorax) to the patient. Moreover, even large volume, or multiple markers can be injected with thin needles making it possible to make markers so large that the surgeon easily can feel it and identify tissue boarders (e.g. cancer) defined with the scope.

The present invention is easy to handle, easy to apply at any position in the body. Furthermore, the present invention is injected with no change in current equipment or procedures. The same equipment that is used for taking biopsies is also used for injection of the present invention. In one embodiment the invention is a liquid prior to injection. The palpable marker composition can hence be injected using thin needles ($\leq$25G) either percutaneously or using an endoscope assisted injection method (EUS, EBUS etc.). In one embodiment the size of the marker can be controlled. This is due to size being based on the injection volume, making it possible to make easy palpable large volume markers. In one embodiment the present invention is visible in relevant imaging modalities (X-ray, MRI and ultrasonography). In another embodiment it is visible in multiple imaging modalities.

In one embodiment the present invention forms a hard crystalline or amorphous solid marker after injection. This allows for the marker to be possible to palpate. The present invention is in one embodiment blue. This implies that visual identification by the surgeon is possible.

In one embodiment, the present invention aims at solving the clinical challenge of making small non-palpable tumors palpable.

In an in-vivo experiment evaluating the palpable marker composition of the present invention it was found to have all suitable characteristics to function as a marker for making soft tissue palpable; In one embodiment the present invention is a liquid prior to injection. In another embodiment the present invention is injectable. In yet another embodiment, small needles may be used. Size of needle may vary; in one embodiment needles of size 25G is used.

The present invention may be colored for easy recognition. In one embodiment the color remains within the marker and do not diffuse out of the marker matrix. In one embodiment the color leaks from the marker into the surrounding tissue.

There are further benefits of the present invention partly due to the phase transition going from liquid to solid complete within 24 h. This feature enables day-to-day procedures in the clinical setting. The experiments show the invention is highly palpable and well defined in vivo. In FIG. 1, sacrificed mice are shown; 20 hours post injection of the palpable marker composition for making soft tissue palpable. The present invention was palpable and easily recognized by surgeons.

There are of course various forms of injection patterns possible and ways of injecting, such as, but not limited to, transcutaneous injection, using a scope (bronchoscope, gastroscope, or any other flexible wired systems used to navigate inside a body), attached to another such system, intracranial injection, inside air and fluent filled organs or cavities (e.g. bladder, stomach). Further, there are various forms of dosing such as, but not limited to, fast injections (bolus), pulling back to needle while injecting, slowly injection on the site, pushing the needle forward, and pump giving a constant pressure for a defined period. Furthermore, there are various devices that may be used such as, but not limited to, needle with 1 or more holes on the side of the needle forming multiple smaller objects, flexible, multiple chamber systems.

Experiment

The aim of this experiment is to prepare a liquid injectable marker, which upon injection solidifies within 24 h to form a palpable marker, which subsequently can be used for directing surgery of non-palpable tumors in e.g. VATS, Furthermore; this experiment aims at investigating how rapid solidification of the marker is achieved in vivo following s.q. injection into healthy NMRI mice.

Principle: Neat lactose octaisobutyrate (LOIB) readily dissolves in anhydrous EtOH to form low viscosity homogenous solutions suitable for injection trough thin needles ($\leq$25G). Injection into soft tissue (hydration) causes efflux of EtOH due to non-solvent induced phase separation (NIPS) which triggers precipitation of LOIB, hence, a solid implant is formed.

Hydrophobic additives can be added to the LOIB:EtOH mixture without compromising the solidification process. Quinizarin Blue (Cas #81-48-1), commonly used to dye degradable sutures, is added to the LOIB:EtOH mixture to dye the implant dark blue for rapid visualization in soft tissue. Furthermore, x-SAIB is added to the LOIB:EtOH mixture to enhance the radiopacity of the material for easy recognition using x-ray based imaging techniques such as CT-imaging.

Materials: The following materials (Table 1) were used to prepare the marker

TABLE 1

Overview of materials used for marker preparation.

| Name | Manufacturer | Cas# | Product# | Purity (Lot# etc) |
|---|---|---|---|---|
| Quinizarin Blue | TCI | 81-48-1 | CI-60725 | >90%, K72CB-CD |
| EtOH | SigmaAlldrich | 64-17-5 | N/A | >99.5% |
| x-SAIB | NCK | N/A | N/A | Lot 71427 |
| LOIB | In-house prep | N/A | N/A | >95% |

Experimental Protocol
Formulation of Marker

The liquid injectable marker for making non-palpable tumors palpable is prepared by weighting the amounts listed in Table 2 below into a 8 mL glass vials to obtain a liquid formulation consisting of LOIB:EtOH:x-SAIB:Quinizarin Blue (69.5:20:10:0.25)

TABLE 2

Amount of materials required for marker preparation.

| Vial# | LOIB (g) | EtOH (mg/mL) | x-SAIB (mg) | Quinizarin Blue (mg) | Mass iodine (mg) | Iodine in gel (m %) |
|---|---|---|---|---|---|---|
| 1 | 3.14 | 900/1.14 | 450 | 11.2 | 189 | 4.2 |

A glass vial with included compounds was heated to approx. 60° C. in a water bath with sonication to form clear homogenous solutions for approximately 30 min with occasional vortexing.

The vial was stored at RT until used.
In Vivo Evaluation of Solidification Rate

Evaluation of the in vivo solidification rate was conducted in healthy NMRI-mice using 3 groups of 3 mice in each—9 mice in total. The marker (200 µL) was injected the upper part of the back using a 25G needle under general anesthesia. Animals were sacrificed after approximately 1-, 3- and 24 h (see FIG. 1) and the implants surgically removed to visually evaluate the hardness for the markers at the given time points and evaluate if the markers can be exploited for making non-palpable tumor recognizable during surgery.
Results Day 1: The marker was prepared by weighting the following amounts of LOIB, EtOH, x-SAIB and Quinizarin Blue as specified in Table 3.

TABLE 3

Amount of each component weighted off for marker preparation.

| Vial# | LOIB (g) | EtOH (mg/mL) | x-SAIB(mg) | Quinizarin Blue (mg) |
|---|---|---|---|---|
| 1 | 3.14 | 900/1.14 | 460 | 14.0 |

Figure 2:
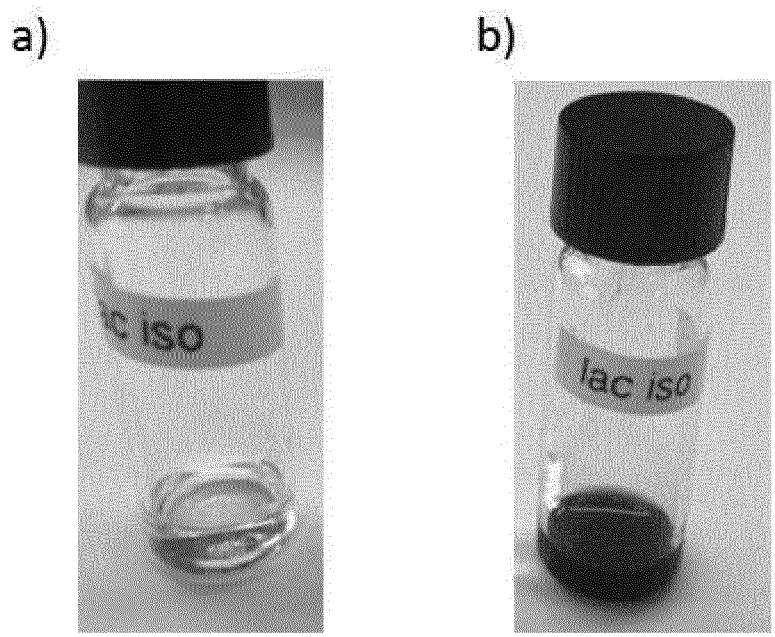
FIG. 2. Liquid gels visualization before/after addition of Quinizarin Blue.

The vial was tightly sealed with parafilm and heated to 60° C. for 30 min with sonication and occasional vortexing to form a dark blue homogenous solution (FIG. 2).

The solution was stored at RT overnight until further use.

Day 2: The liquid marker was pulled into a disposable 1 mL syringe using a 20G needle and injected (200 µL) at the upper back on 9 healthy NMRI-mice (40-50 g each, 3 groups; A, B and C of 3 mice each) using a 25G needle (27G was tried but viscosity to high) under general anesthesia.

Group A (n=3) was sacrificed 1 h p.i. (post injection) and marker morphology was analyzed by surgical removal of the marker. The markers were identified as sticky hard gum-like markers. These were palpable and not completely solidified after 1 h.

Group B (n=3) was sacrificed 3 h p.i. and marker morphology was analyzed by surgical removal of the marker. Gels were identified as sticky hard gum-like markers. These were palpable and not completely solidified after 3 h.

Group C (n=3) was housed overnight.

Figure 3:
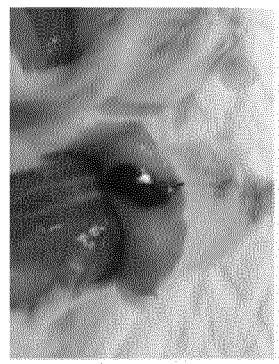
FIG. 3: sacrificed mice (n=3) are shown; 20 hours post injection of the palpable marker composition for making soft tissue palpable.
Figure 3:
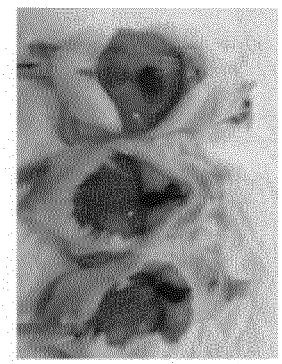
Figure 3:
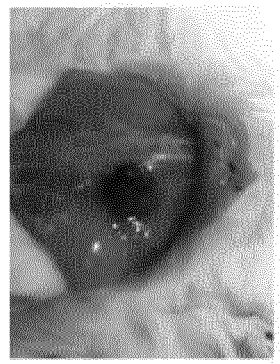
Figure 3:
Figure 3:
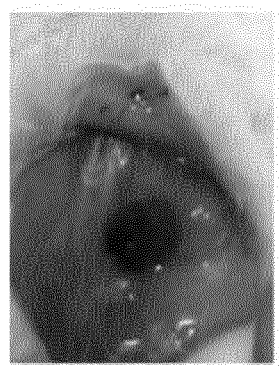
Figure 3:
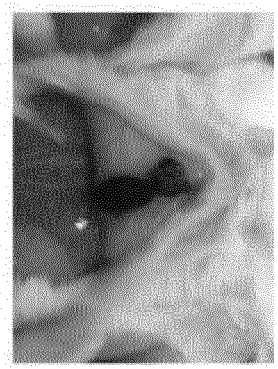
Figure 3:

Day 3:

Group C (n=3) was sacrificed 20 h p.i. and marker morphology was analyzed by surgical removal of the marker (see images in FIG. 3). Gels were identified as solid and very hard markers with a sticky inner-part. These were highly palpable and were judge to fully fulfill the intended use of the marker; e.g. making non-palpable tissue palpable.

In conclusion, the blue colored injectable gel evaluated in this experiment was found to have suitable characteristics to function as a marker for making soft tissue palpable. The present invention may in one embodiment comprise the features:

Liquid prior to injection.

Injectable through small 25G needles.

Colored for easy recognition. Color remains within the gel marker and did not diffuse out of the marker.

Phase transition going from liquid to solid complete within 24 h enabling day-to-day procedures in the clinical setting.

Highly palpable and well defined in vivo.

Example 2: Synthesis of Carbohydrate Esters

General Experimental Conditions:

All reactions were carried out under inert atmosphere ($N_2$). Water sensitive liquids and solutions were transferred via syringe. Water used for washing of the isolated products was in all cases MilliQ water. Organic solutions were concentrated by rotary evaporation at 30-60° C. under 200-0 mbar. Thin layer chromatography (TLC) was carried out using aluminum sheets pre-coated with silica 60F (Merck 5554). The TLC plates were inspected under UV light or developed using a cerium ammonium sulphate solution (1% cerium (IV) sulphate and 2.5% hexa-ammonium molybdate in a 10% sulfuric acid solution).

Reagents:

Chemicals were all purchased from Sigma Aldrich and were used as received. Dry pyridine was obtained by drying over molecular sieves (4 Å) for 2-3 days prior to use.

Instrumentation:

Nuclear Magnetic Resonance (NMR) was conducted on a Bruker Ascend™ 400 MHz—operating at 401.3 MHz for $^1$H and 100.62 MHz for $^{13}$C—with a 5 mm H—Broadband Dual Channel z-gradient Prodigy cryoprobe at 298 K using the residual solvent as internal standard. All coupling constants (J) are expressed in Hz. The FID files were processed in Mnova Suite version 8.1.4. In $^1$H-NMR spectra of α,β0 anomeric mixtures, the integral of H-1 of the most abundant anomer was always set to 1.0, and the percentage of each anomeric species was calculated from the integral ratio of H-1α and H-1β. MALDI-TOF MS was conducted on a Bruker Autoflex Speed™ mass spectrometer. The matrix used for MALDI-TOF was a mixture of 2,5 dihydroxy benzoic acid (DHB) spiked with sodium trifluoroacetate in ethanol (60 mg/mL).

General Experimental Procedure for Synthesis of Carbohydrate Esters

Carbohydrates (di- and trisaccharides, typically 10-100 g) were suspended in dry pyridine under inert atmosphere ($N_2$). Hereafter, acetic, propionic or isobutyric anhydride (2.2 eq. pr. hydroxyl group) was carefully added. Then, a catalytic amount of DMAP (0.1 eq.) was added. The reactions were heated to 48° C. overnight and then continued for ~24 hours at room temperature until TLC and MALDI-TOF showed complete acylation of the starting material. The reactions were concentrated under reduced pressure and co-evaporated with toluene. The concentrates were dissolved in $CHCl_3$ and washed with $NaHCO_3$ (aq.) (3×), brine (1×) and water (2×). The organic phases were dried with $MgSO_4$ (s), filtered, concentrated under reduced pressure and dried in vacuo. Yields and reported spectra of individual sugar esters can be found below.

Raffinose Undecaisobutyrate

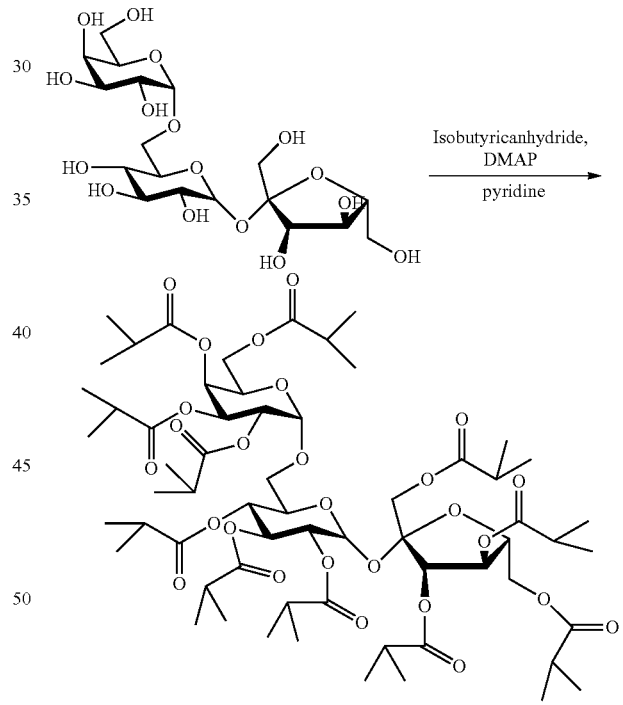

Yield: 84.3%. $^1$H NMR (400 MHz, $CDCl_3$) δ 5.58-5.44 (m, ~4H), 5.49-5.38 (m, 1H), 5.42-5.29 (m, 1H), 5.28 (t, J=9.8 Hz, 1H), 5.18-5.07 (m, 2H), 4.89 (dd, J=10.4, 3.6 Hz, 1H), 4.41-4.30 (m, 1H), 4.31-4.14 (m, 4H), 4.11-3.99 (m, 4H), 3.75 (dd, J=11.7, 3.4 Hz, 1H), 3.58 (dd, J=11.8, 1.9 Hz, 1H), 2.71-2.34 (m, 11H), 1.24-1.08 (m, ~66H). $^{13}$C NMR (101 MHz, $CDCl_3$) δ 176.6 (2C), 176.5, 176.1 (3C), 176.0, 175.9, 175.8, 175.5, 175.1, 103.6, 97.0, 90.0, 78.7, 75.3, 74.6, 70.1, 69.8, 69.6, 68.1, 67.8 (2C), 67.7, 66.6, 65.9, 64.2, 62.9, 61.4, 34.2, 34.0 (5C), 33.9 (4C), 33.8, 19.3 (2C), 19.1 (3C), 19.0 (7C), 18.9 (6C), 18.8, 18.7, 18.5, 18.4. MALDI TOF-MS: Calc [M+Na]⁺: 1298.43. Found: 1298.46.

Trehalose Octaisobutyrate

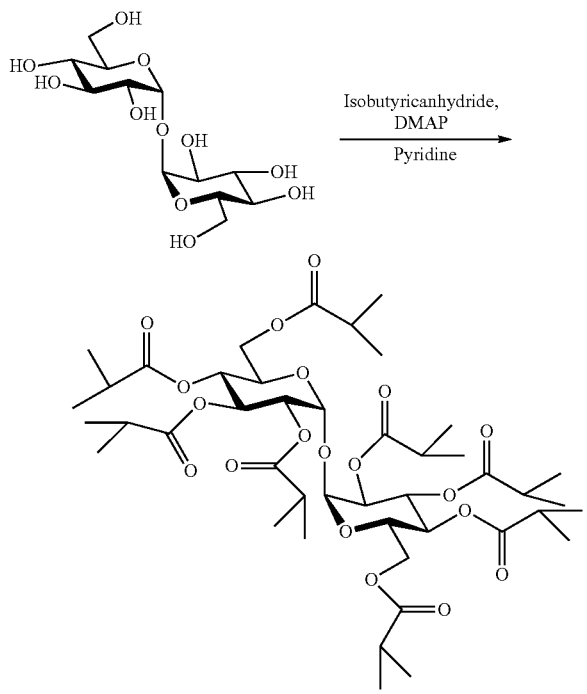

Yield: 91%. $^1$H NMR (400 MHz, CDCl$_3$) δ 5.55 (t, J=9.8 Hz, 2H), 5.36 (d, J. 3.8 Hz, 2H), 5.10 (t, J=9.9 Hz, 2H), 5.03 (dd, J=10.1, 3.8 Hz, 2H), 4.08 (m, 4H), 3.91 (ddd, J=10.4, 5.5, 2.1 Hz, 2H), 2.63-2.52 (m, 4H), 2.48 (m, 4H), 1.17 (m, 24H), 1.13-1.07 (m, 24H). $^{13}$C NMR (101 MHz, CDCl$_3$) δ 176.7 (2C), 175.9 (2C), 175.7 (2C), 175.4 (2C), 90.5 (2C), 70.2 (2C), 69.8 (2C), 68.6 (2C), 68.0 (2C), 61.6 (2C), 34.1 (2C), 34.0 (4C), 33.9 (2C), 19.1 (2C), 19.0 (8C), 18.9 (4C), 18.8 (2C). MALDI TOF-MS: Calc [M+Na]+: 926.02. Found: 925.97.

α,β Lactose Octaisobutyrate

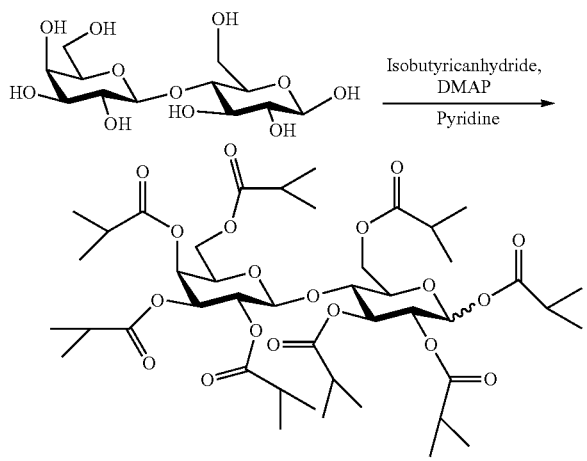

Yield: 89.5% (mixture of anomers: ~30% α and ~70% β). $^1$H NMR (400 MHz, Chloroform-d) δ 6.26 (d, J=3.8 Hz, 0.4H, H-1α), 5.68 (d, J=8.3 Hz, 1H, H-1β), 5.48 (dd, J=10.3, 9.3 Hz, 0.4H), 5.40-5.34 (m, 2H), 5.27 (t, J=9.5 Hz, 1H), 5.18-5.00 (m, 3H), 5.03-4.91 (m, 2H), 4.50-4.41 (m, 3H), 4.24-4.02 (m, ~4H), 3.95 (ddd, J=10.1, 3.8, 1.7 Hz, 0.4H, H5α), 3.91-3.80 (m, 3H), 3.70 (ddd, J=9.9, 4.5, 2.0 Hz, 1H, H5β), 2.70-2.32 (m, ~11H), 1.26-1.01 (m, ~68H). MALDI TOF-MS: Calc [M+Na]$^+$: 926.02. Found: 925.70.

Figure 4:
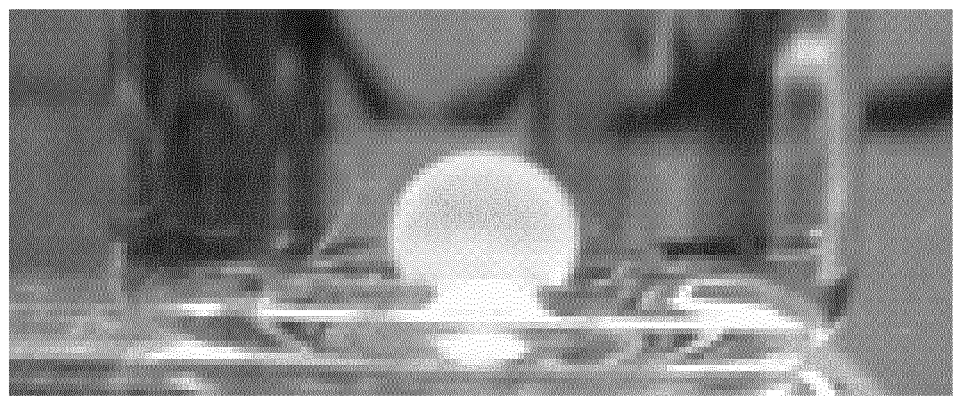
FIG. 4: Visual inspection of typical carbohydrate ester material (here: lactose octaisobutyrate) after injection into PBS buffer.

Example 3: Injectability of Carbohydrate Ester Formulations 210 mg of the following sugar esters: α,β-Lactose octaisobutyrate, trehalose octaisobutyrate and raffinose undecaisobutyrate were mixed with 20% EtOH by heating to 37° C., vortexing and ultrasonication. 50-80 µL of the resulting formulations were then injected into 2 mL of PBS buffer using 25 G needles. All formulations formed solid markers within 1 hour after injection into PBS (see FIG. 4 with representative example).

Example 4: Coloring Palpable Marker Formulations and Marker Radiopacity

A screening procedure was conducted with different marker compositions (see Table 1) in order to verify possible of coloring of the markers and to demonstrate that the coloring additive remain associated with the markers after injection into aqueous media. Coloring of the markers was in this example demonstrated with the synthetic anthraquinone dye D&C Violet No. 2. Radiopacity of the markers was introduced by adding the iodinated component x-SAIB to the markers in order to increase the electron density of the marker.

TABLE 1

Specifications for preparation of Formulation #1-3. LOIB: Lactose octaisobutyrate. x-SAIB: iodinated component.

| | Composition (w/w %) | | | | |
|---|---|---|---|---|---|
| Formulation# | LOIB | EtOH | x-SAIB | D&C Violet No. 2 | Iodine content |
| 1 | 69.95 | 20 | 10 | 0.05 | 4.2 |
| 2 | 69.9 | 20 | 10 | 0.10 | 4.2 |
| 3 | 69.8 | 20 | 10 | 0.20 | 4.2 |

Figure 5:
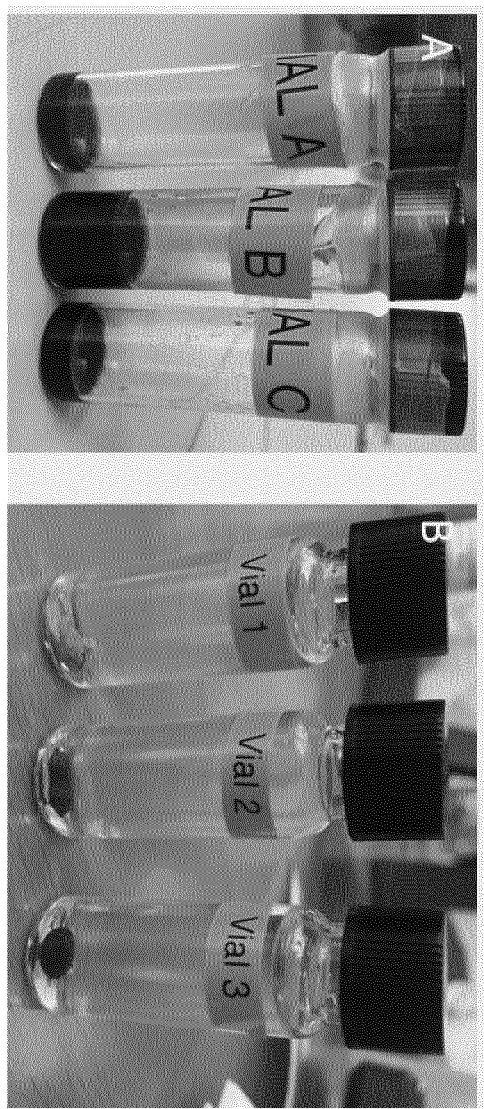
FIG. 5: Marker solutions (Vial #1-3) markers of approximately 50 µL formed in MQ-$H_2O$ FIG. 6. CT-scan of palpable markers casted into gelatin in a thorax phantom. Markers were analyzed using the semi-automated contouring software in Eclipse with a lower threshold of 200 HU.

Each formulation was heated to 60° C. on a water bath with occasional vortexing for 15 min. The samples were completely dissolved and homogenous (visual inspection) after 15 min (FIG. 5A).

Small markers of approximately 50 uL were prepared by injection into 4 mL glass vials filled with MQ-H$_2$O using a 25G needle to enable ethanol efflux and marker solidification. The coloring intensity of each marker and possible release of dye to the aqueous media was visually assessed. A clear increase in coloring intensity as observed from Formulation A to Formulation C and no sign of release of dye was observed in any case (FIG. 5B).

Figure 6:
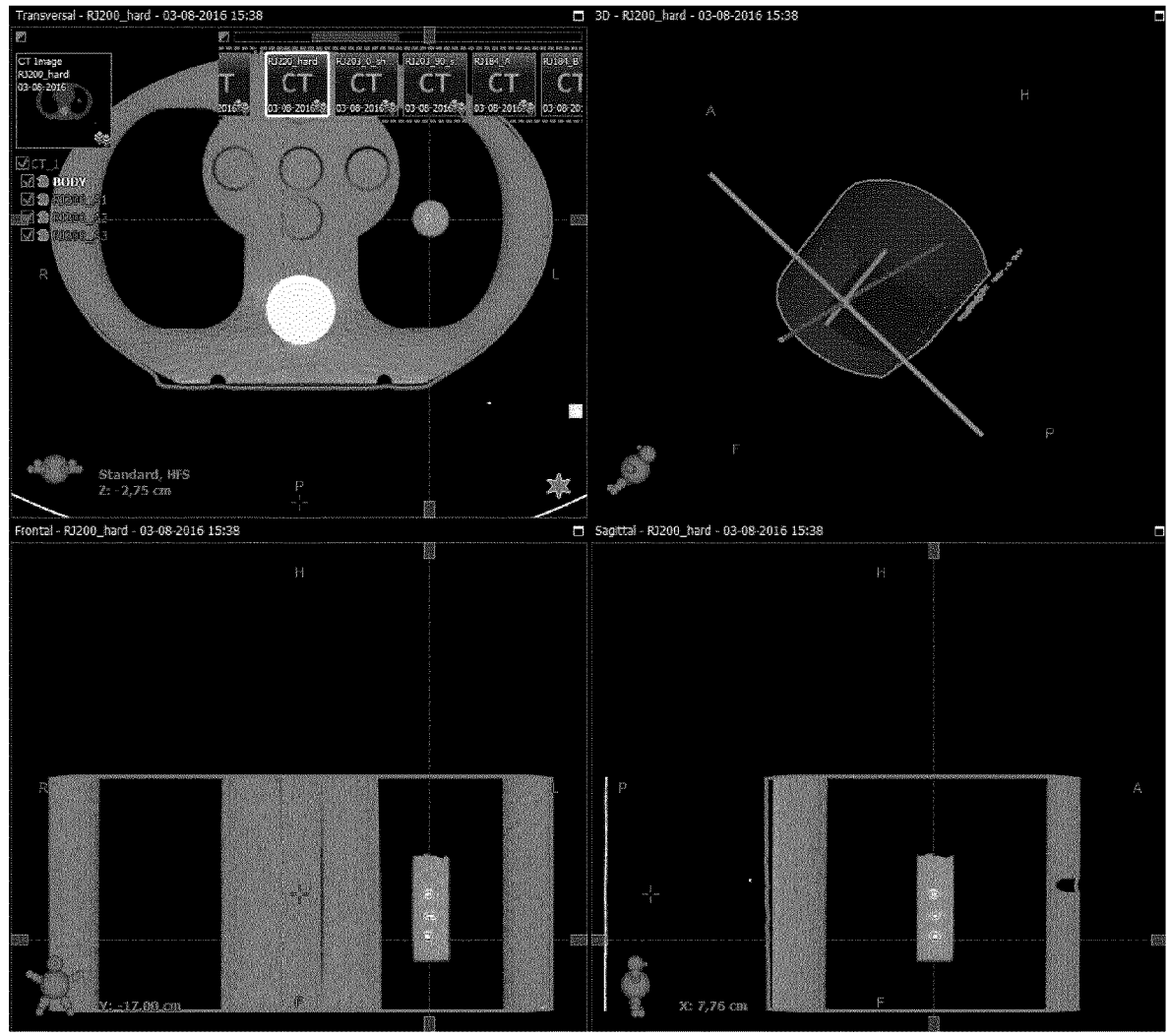

The radiopacity of the markers in CT-imaging was evaluated by casting the formed markers from each formulation (50 uL each, n=3) into 10 w/w % gelatin in a low density PE tube. The plastic tube containing the palpable markers was placed in a thorax phantom using a clinical CT-scanner, slice thickness 1 mm. The radiopacity of the markers was analyzed using the semi-automated contouring software in the Eclipse software (Varian) using a lower threshold of 200 HU. Markers were clearly visible in the recorded CT-scan;

mean contrast±SD (HU); Formulation 1; 419±155, Formulation 2; 457±204 and Formulation 3; 524±209—see FIG. 6.

Example 5: Marker Hardness Following Subcutaneous Implantation in Mice

Three marker formulations based on either raffinose undecaisobutyrate (RI), lactose octaisobutyrate (LOIB) or trehalose octaisobutyrate (TI) were prepared in the ratios listed in Table 2.

TABLE 2

Specifications for preparation of Formulation #1-3. Lactose isobutyrate (LOIB), trehalose isobutyrate (TI) and raffinose isobutyrate (RI)

| Formulation# | Composition (w/w %) | | | | |
|---|---|---|---|---|---|
| | LOIB | TI | RI | EtOH | D&C Violet No. 2 |
| 1 | 79.75 | — | — | 20 | 0.25 |
| 2 | — | 79.75 | — | 20 | 0.25 |
| 3 | — | * | 79.75 | 20 | 0.25 |

Figure 7:
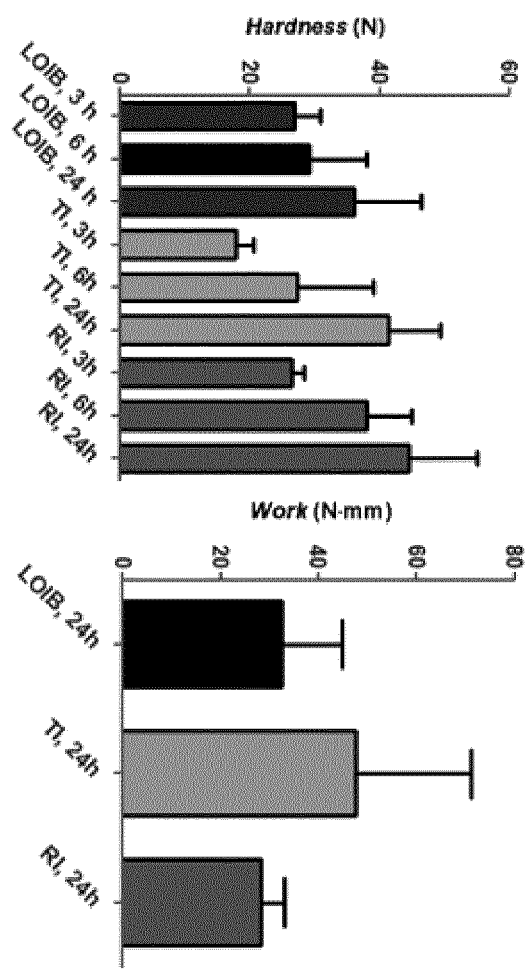
FIG. 7. Texture analysis of markers of lactose isobutyrate (LOIB), trehalose isobutyrate (TI) and raffinose isobutyrate (RI) (N=3, Mean±SD) showing the max force required to break the markers after 3, 6 and 24 hours subcutaneously in mice along with the amount of work required to break the markers after 24 hours in the mice. Images of LI markers after 24 h show well-defined, fully hard markers that are easily palpable and intact when removed from the subcutaneous compartment. The dye furthermore stayed in the markers, enabling visual guidance during a surgical procedure.
Figure 7:
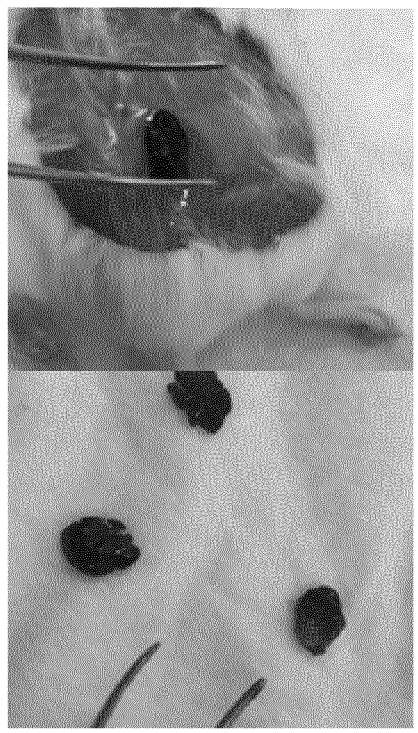

Each formulation (100 uL) was injected subcutaneously in BalbC mice (n=3) under general anesthesia. Texture analysis of the markers was acquired after excision at 3, 6 and 24 h post injection. Texture analysis of was conducted on a TA.XT plus texture analyzer applying a 50 N load cell and a cylindrical compression probe with 2 mm diameter. Test speed was 0.5 mm/s, and maximum compression of the materials was 50%. Peak Force (N) for first penetration of the materials was recorded as a measure of hardness. Work (N·mm) was retrieved as the areas under the compression curves as a measure of material toughness. Results are shown in FIG. 7. All markers could easily be removed from the subcutaneous compartment of the mice and the marker hardness for each formulation was found to increase over time. Additionally, the dye was found to remain within the markers throughput the experiment.

Example 6: Viscosity of Marker Formulations

The viscosity and density of marker formulations based on LOIB, x-SAIB, EtOH and D&C Violet 2 in the ratios listed in Table 3 were evaluated.

TABLE 3

Specifications for preparation of Formulation #1-4.

| Formulation# | Composition (w/w %) | | | |
|---|---|---|---|---|
| | LOIB | x-SAIB | EtOH | D&C Violet No. 2 |
| 1 | 49.9 | 30 | 20 | 0.10 |
| 2 | 51.9 | 30 | 18 | 0.10 |
| 3 | 53.9 | 30 | 16 | 0.10 |
| 4 | 55.9 | 30 | 14 | 0.10 |

Figure 8:
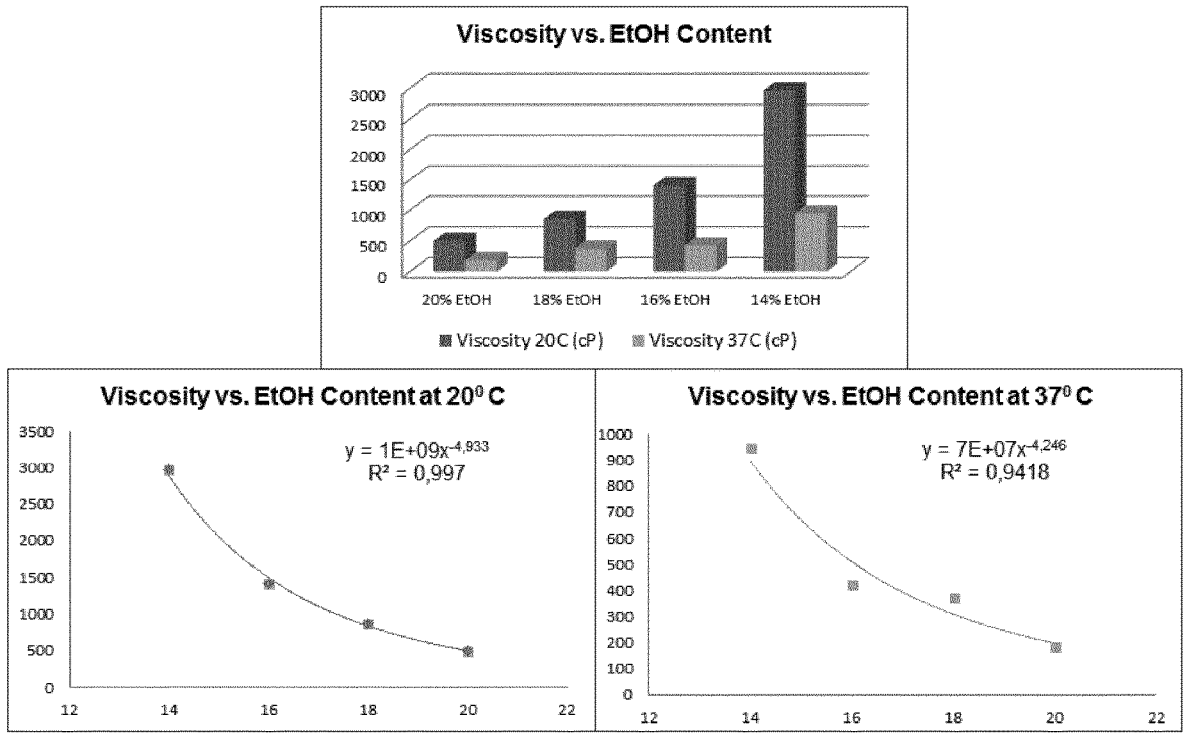
FIG. 8. Relationship between viscosity of palpable marker formulations as a function of EtOH content at 20° C. and 37° C.

All formulations were obtained as dark blue homogenous liquids with increasing viscosity as the ethanol content reduced from 20.0 w/w % to 14.0 w/w %. The viscosity of each formulation was measured using a Brookfield LVDV rotation viscosimeter in small sample adaptor spindle SC-4-31 at 20° C. and 37° C. Values were recorded after 5 minutes rotation. 20° C. was chosen to mimic the temperature during the marker placement procedure in the clinic, and 37° C. was chosen as this resembles the physiological temperature. The results are shown in FIG. 8. A clear correlation between the ethanol content in the formulations and the viscosity was observed.

Figure 9:
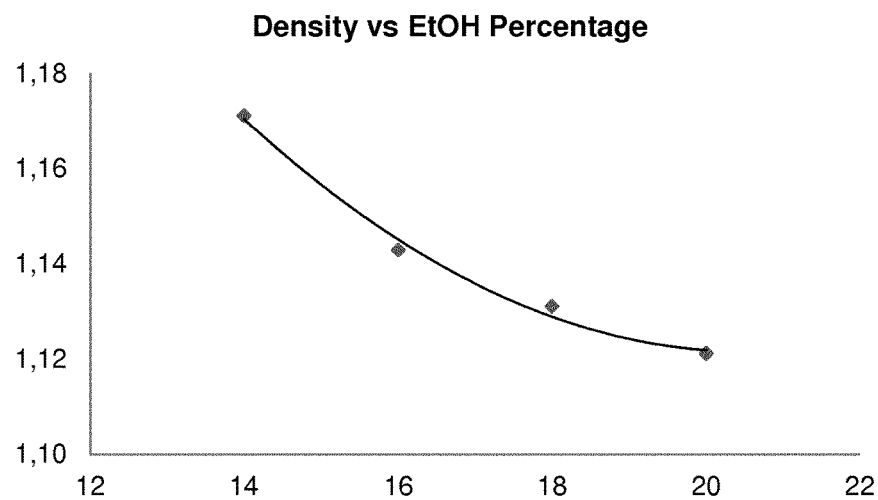
FIG. 9. Density of palpable marker formulations vs. ethanol percentage.

The density of each of the four formulations were measured using a measuring flask (V=1.00 mL). The flask was weighted on the analytical scale and the density calculated based on the mass change. The obtained results are given in FIG. 9.

Example 7: Injectability and Backpressure of Palpable Marker Formulations

The injectablity of three formulations based on LOIB and EtOH in the ratios listed in Table 3 were evaluated.

TABLE 3

Specifications for preparation of Formulation #1-3.

| Formulation# | Composition (w/w %) | |
|---|---|---|
| | LOIB | EtOH |
| 1 | 80 | 20 |
| 2 | 82 | 18 |
| 3 | 85 | 15 |

Figure 10:
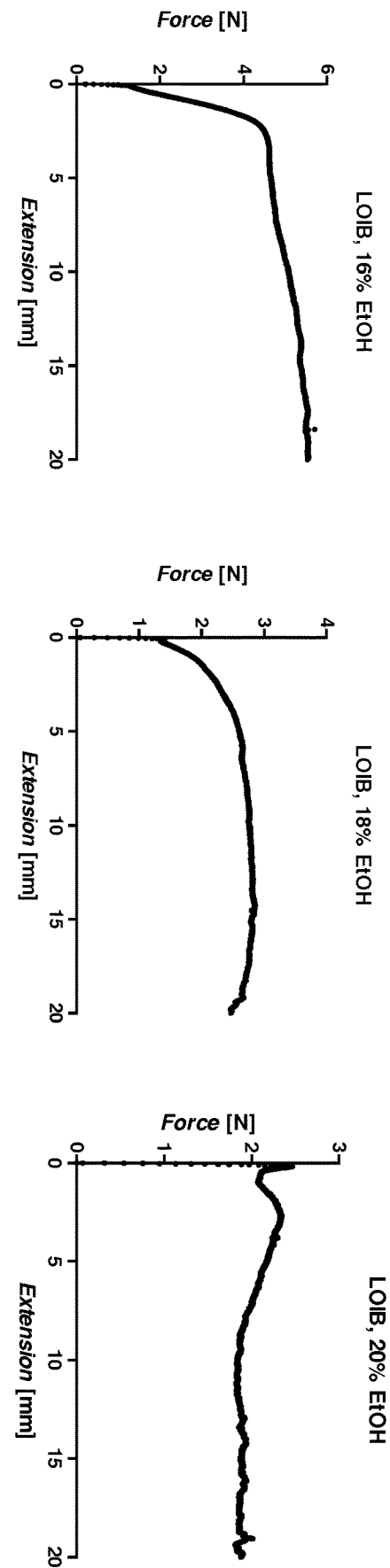
FIG. 10. Force-extension curves of injection from 1 mL syringes through 21 G needles of different formulations (LOIB+16, 18 and 20% EtOH). In the first part of the curve, the solution showed a weak elastic response until constant flow was obtained. The smaller the w/w % of EtOH, the higher the viscosity, and therefore the higher the plateau-force necessary to obtain a stable flow of the solution out of the syringe.

Each formulation was pulled into a 1 mL syringe equipped with a Luer lock connection (piston diameter: 4.40 mm) mounted with 21 G needle. The syringes containing each of the formulations were installed in a syringe test fixture per ISO-7886-1 mounted on an Instron mechanical tester. Using a constant rate ~0.4 mL of the formulation was injected through the needle using a flat probe to advance the syringe piston (probe diameter 4.6 cm, Load cell: 500 N, test speed 5 mm/min). Force-extension diagrams were recorded in real-time. The results are shown in FIG. 10. All formulations were easily injectable with increasing back-pressure as the ethanol content was decreased.

| LOIB, 16% EtOH | LOIB, 18% EtOH | LOIB, 20% EtOH |
|---|---|---|
| Backpressure (KPa) 329.32 | Backpressure (KPa) 179.30 | Backpressure (KPa) 133.20 |

Example 8: X-Ray Crystallography Characterization of Palpable Markers

The atomic and molecular structural features of palpable marker compositions listed in Table 4 and the pure raw materials LOIB and x-SAIB (10-30% x-SAIB, 18% EtOH, 0.1% quinizarin blue in LOIB) were investigated by X-ray crystallography.

TABLE 4

Specifications for preparation of Formulation #1-3.

| Formulation# | Composition (w/w %) | | | |
|---|---|---|---|---|
| | LOIB | x-SAIB | EtOH | D&C Violet No. 2 |
| 1 | 71.9 | 10 | 18 | 0.10 |
| 2 | 61.9 | 20 | 18 | 0.10 |
| 3 | 51.9 | 30 | 18 | 0.10 |

Figure 11:
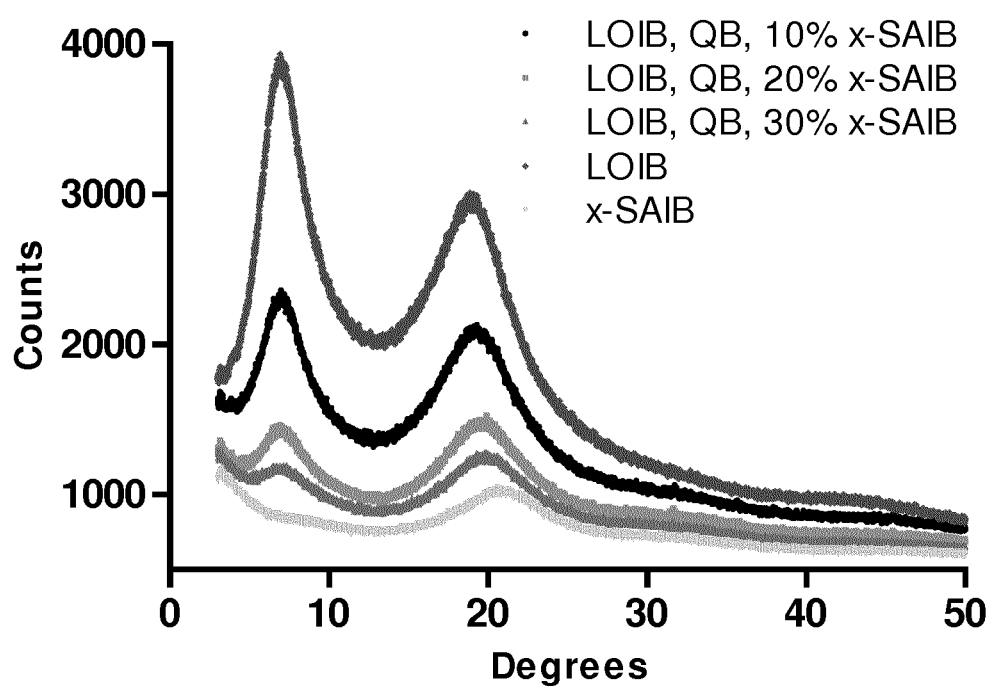
FIG. 11. X-ray crystallography of palpable marker compositions containing 10-30% x-SAIB with pure SAIB and lactose octaisobutyrate (LOIB) as reference controls. All materials show clear evidence of amorphous structure (broad diffraction peaks).

X-ray crystallography was conducted on 20 mg of powdered samples on a Huber G670 X-ray diffractometer for 10 minutes from 3°-100°. X-ray crystallography analysis supported that the raw materials and the solid markers exhibited an amorphous structure as illustrated in FIG. 11.

Example 9: Mechanical Properties of Palpable Markers Formed In-Vitro

The mechanical properties of palpable markers formed in vitro with the composition given in Table 5 were evaluated by plate compression.

TABLE 5

Specifications for preparation of Formulation #1-3.

| | Composition (w/w %) | | | |
|---|---|---|---|---|
| Formulation# | LOIB | x-SAIB | EtOH | D&C Violet No. 2 |
| 1 | 51.9 | 30 | 18 | 0.10 |

Figure 12:
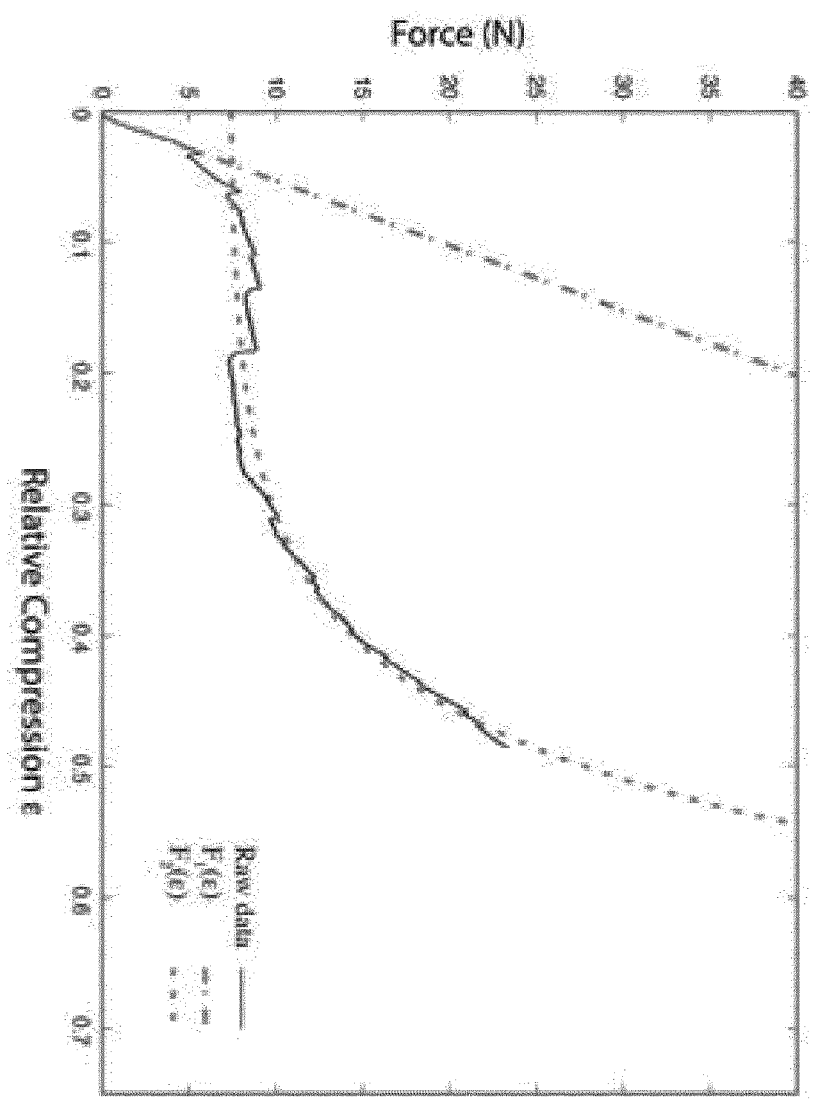
FIG. 12. Example of Instron compression data analysed by fitting to $F_1(\varepsilon)$ and $F_2(\varepsilon)$ and corresponding pictures of the marker before and after the compression cycle. The shown marker was incubated 7 days in milliQ water prior to mechanical testing using a test speed of 1 mm/min.
Figure 12:
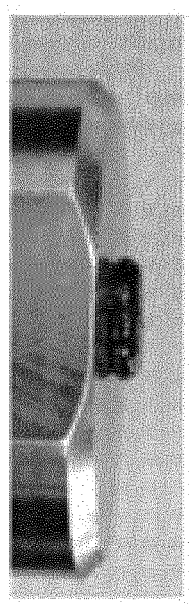
Figure 12:
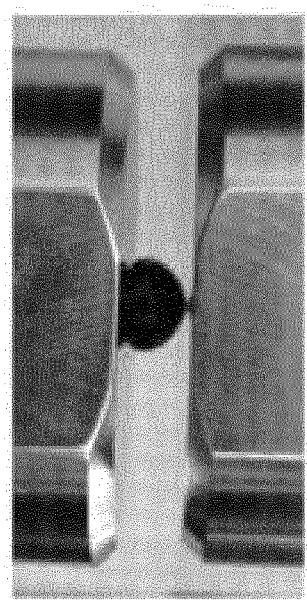
Figure 13:
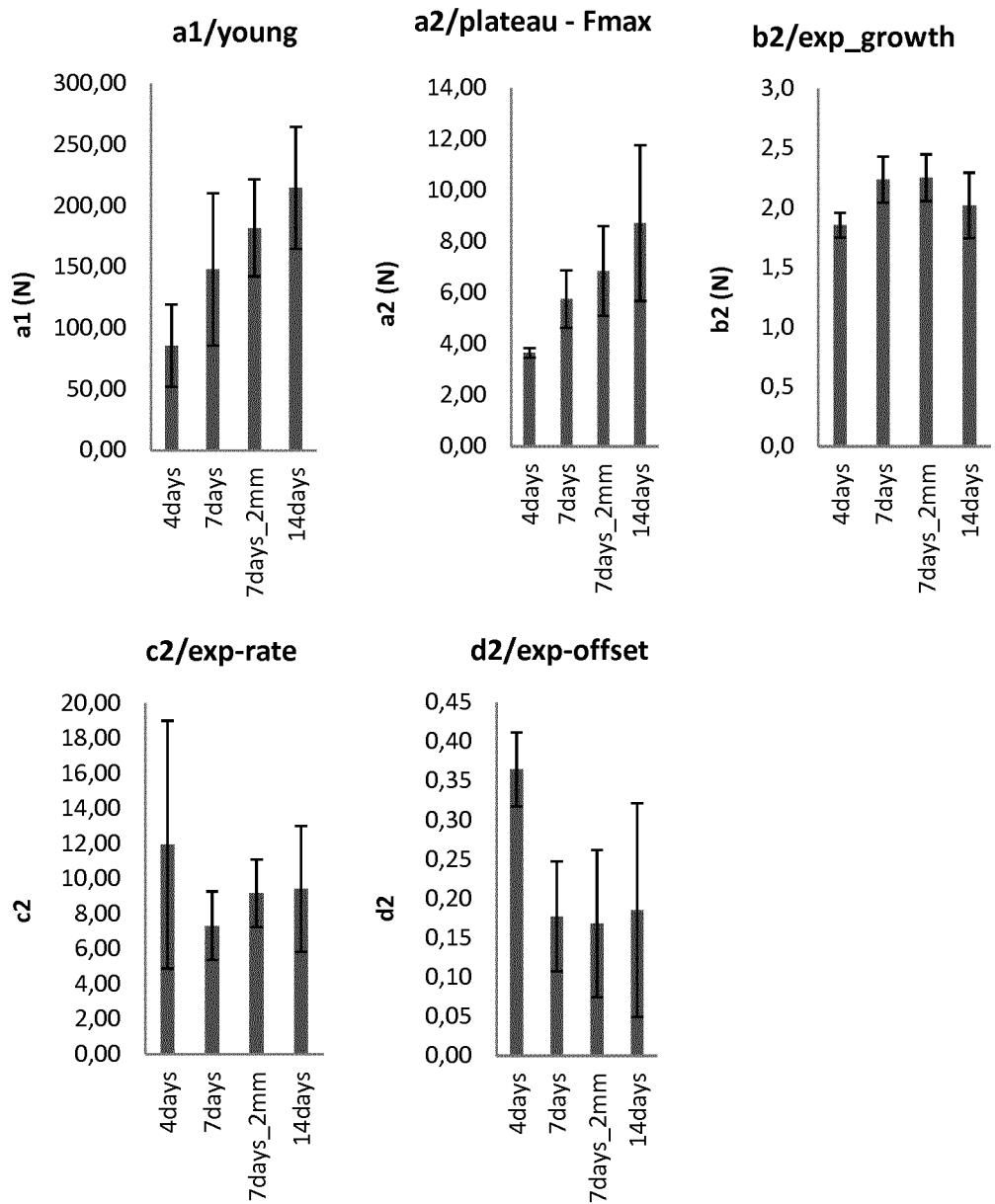
FIG. 13. Data compilation of marker compressions conducted after 4, 7 and 14 days of EtOH efflux (N=6, Mean±SD). The compression data (example shown in FIG. 11) was analyzed using the fitting expressions $F_1$, and $F_2$. Compression speed was 1 mm/min except for the 7 days_2 mm data, where compression was 2 mm/min. a1: young's modulus (stiffness), a2 (Fmax): hardness, b2 and c2: expo-nential response coefficients, d2: crossover point from plateau response to exponential growth.

~300 uL of palpable marker Formulation #1 was injected in 6 replicates in MQ water (exchanged day 1, 3 and 7) and kept at 37° C. Mechanical properties of the markers were characterized by mechanical testing at 4, 7 and 14 days after injection. Marker mechanical response was measured by plate compression on an Instron mechanical tester (50 N load-cell, 4.6 cm diameter compression plate, test speed: 1 mm/min). The initial height of the marker ($h_i$) was recorded before start of the experiment, and the relative compression computed as $\varepsilon = \Delta x / h_i$ where $\Delta x$ change in distance between the flat probes. The resulting force-extension curves were analysed by fitting to the expressions $F_1$ and $F_2$. $F_1 = a_1\varepsilon + b_1$, where $a_1$ describes the marker's initial linear response (relates to Young's module) and $b_1$ is the offset. The plateau and exponential response regions are analyzed by fitting the expression: $F_2 = a_2 + b_2 \exp(c_2(\varepsilon - d_2))$, where $a_2$ is the plateau force (maximal force before exponential response), $b_2$ is the magnitude of the exponential response, $c_2$ is the exponential rate coefficient and $d_2$ denotes the crossover from linear or plateau response to the exponential response region (see FIG. 12 for example). The results are shown in FIG. 13. Young's modulus (proportional to $a_1$) and the plateau force ($a_2$) increase as function of EtOH efflux time and do not reach a plateau within the timeframe of the current experiment, i.e. the markers do not reach their maximal hardness within the 14 days of incubation in-vitro. The characteristics of the third compression mode, exponential response, appears to be independent of efflux time, only the force level at which it occurs ($a_2$) differs.

Example 10: In-Vivo Characterization of Palpable Markers in a Porcine Model

Palpable markers with the composition listed in Table 6 were evaluated in a porcine model with high clinical translational value.

TABLE 6

Specifications for preparation of Formulation #1-5.

| | Composition (w/w %) | | | |
|---|---|---|---|---|
| Formulation# | LOIB | x-SAIB | EtOH | D&C Violet No. 2 |
| A | 71.9 | 10 | 18 | 0.1 |
| B | 61.9 | 20 | 18 | 0.1 |
| C | 51.9 | 30 | 18 | 0.1 |
| D | 49.9 | 30 | 20 | 0.1 |
| E | 53.9 | 30 | 16 | 0.1 |

Studies of in-vivo injectability, radiopacity and palpability of palpable markers was performed in two slaughter swine (4 months old, body weight >40 kg). Pigs were chosen as model due to similar anatomy and size compared to humans. Injection of the marker formulations (see Table 6) was conducted using real-time fluoroscopy guidance. CT-imaging was conducted using a Siemens SOMATOM Emotion CT scanner (130 kVp, slice thickness of 2 mm, FOV=variable) and fluoroscopy videos were recorded using a GE Medical Systems OEC-09TH C-arm (automatic exposure control).

Figure 14:
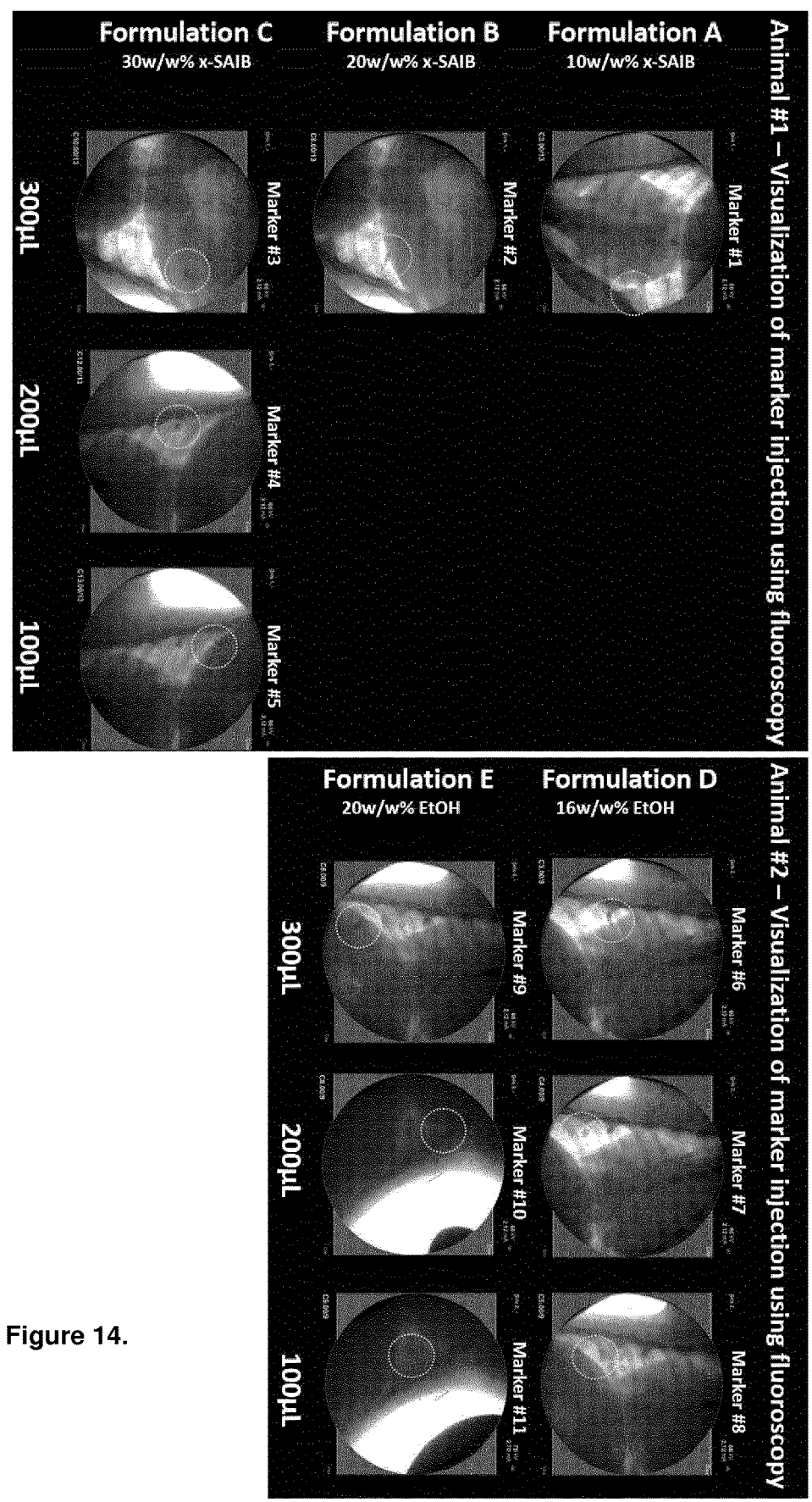
FIG. 14. Marker placement visualized using with real-time fluoroscopy. All injected marker formulation were visible in fluoroscopy during placement.

Formulation #A-C (300 uL) were injected percutaneously directly into healthy lung tissue approximately 1-4 cm from the pulmonary pleura using a Vet Premium needle (22G, I=76 mm, Henck Sass Wolf) in order to evaluate the optimal radiopacity for easy marker visualization in real-time fluoroscopy (FIG. 14). Formulation #C was additionally used to form smaller markers (100 uL and 200 uL) in order to evaluate the effect of marker volume on marker palpability. Furthermore, formulations with increasing (Formulation #D) and decreasing (Formulation #E) ethanol content was injected into healthy lung tissue in order to evaluate the effect on ethanol content on marker palpability (FIG. 14). Following all injections and approx. 24 h post injection CT scans were acquired in order to evaluate marker 3D shape, marker visibility (HU) and interday marker positional stability.

Figure 15:
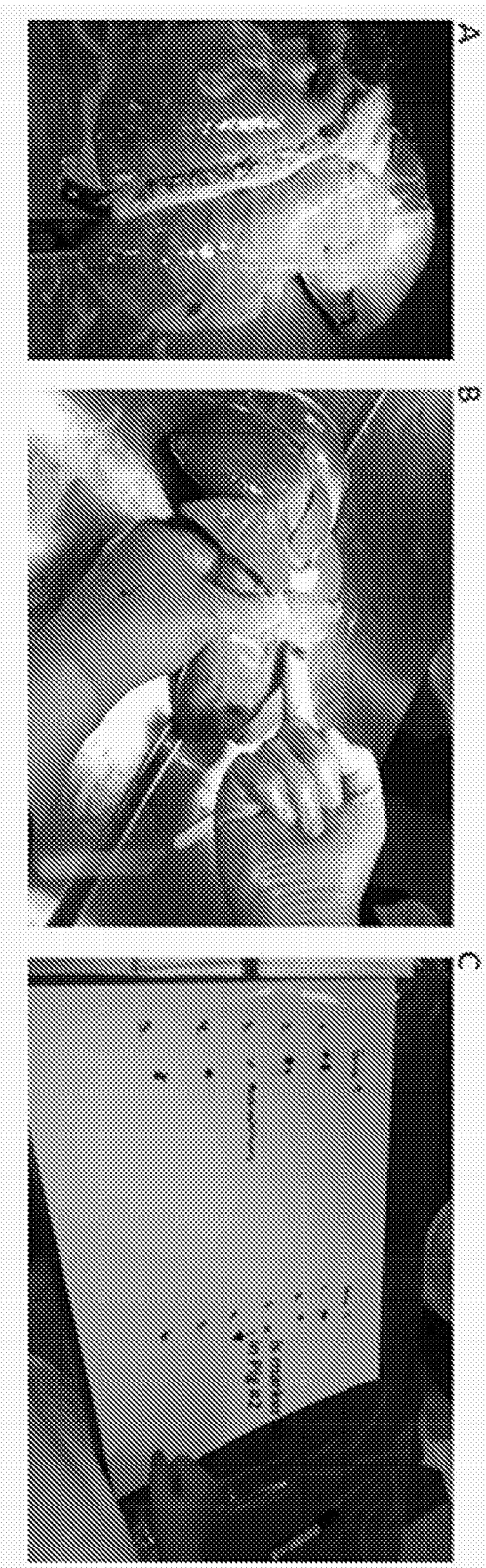
FIG. 15. A) Lung segment with palpable marker visible in the periphery of the left lung. B) Palpable marker removed in a single piece during surgery. C) Combined markers collected from both animals during surgery.

Approximately 24 h post injections both animals were sacrificed and the thorax region was surgically opened and the markers were identified by palpation and visual inspection if placed in close proximity to the pleura. Following palpation with the lungs intact in the thorax region, the lungs and heart were removed from both animals and placed on the surgical table. Again, markers were palpated and identified markers removed from the lung tissue using a scalpel (FIG. 15).

Generally, all markers could be visualized in real-time fluroscopy during injection but 30 w/w % x-SAIB proved optimal for easy recognition. All markers irrespectively of x-SAIB content resulted in excellent visibility on CT images with a minimal degree of image artifacts. Markers formulated with 16-18 w/w % EtOH provided well-defined markers with minimal spreading into surrounding soft tissue. Markers with an injection volume of 200-300 μL proved superior compared to smaller injections volume in creating highly palpable objects. The amount of dye (0.10 w/w %) was sufficient to clearly distinguish markers from tissue and facilitate easy marker localization. Furthermore, coloring of the markers was preferred for easy marker removal during surgery. Markers were in all cases rigid and could be removed from the tissue 24 h post injection.

Example 11: Visualization of Palpable Markers Using Ultrasonography

The visibility of palpable markers with the composition listed in Table 7 in ultrasonography was evaluated in a breast equivalent gelatin based phantom.

TABLE 7

Specifications for preparation of Formulation #1

| | Composition (w/w %) | | | |
|---|---|---|---|---|
| Formulation# | LOIB | x-SAIB | EtOH | D&C Violet No. 2 |
| 1 | 51.9 | 30 | 18 | 0.10 |

Palpable markers (100 μL and 300 μL) were prepared from Formulation #1 by injection into glass vials (30 mL) containing MQ-H$_2$O (25 mL, ~50° C.) using either a 0-200 μL high precision Hamilton syringe or a standard 1 mL disposable syringe with Luer-lock using a 25G needle.

Following marker injection, the markers were stored at 37° C. and the aqueous solution was exchanged once one day after marker injection to remove ethanol.

Markers were casted into a gelatin matrix (10 w/w %) containing NaN$_3$ (0.1 w/w %) and 20 μm cellulose particles (0.5 w/w %) to mimic tissue scattering normally observed in breast tissue. The palpable markers were carefully placed approximately 3 cm apart at a depth of approx. 37 mm and gelatin matrix allowed curing overnight at 5° C. prior to marker visualization using ultrasonography.

Figure 16:
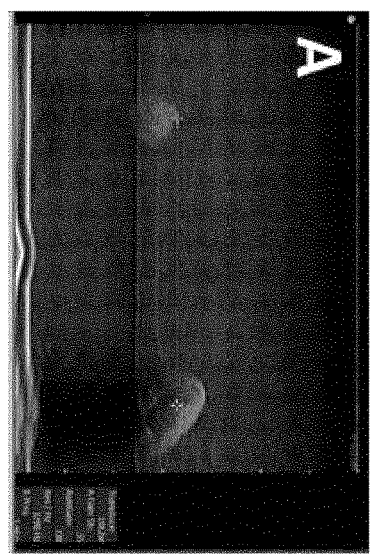
FIG. 16. Ultrasound imaging of palpable markers in a breast equivalent phantom. A; Both markers separated by approx. 3 cm; B) V=100 µL and C) V=300 µL.
Figure 16:
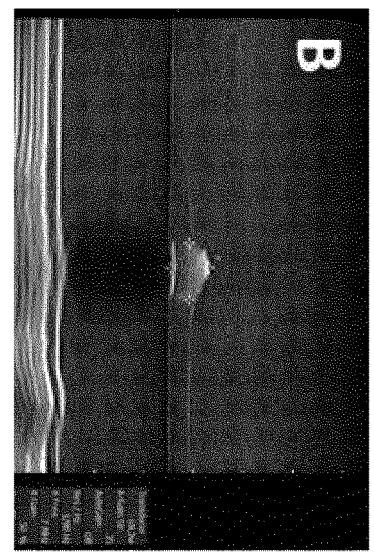
Figure 16:
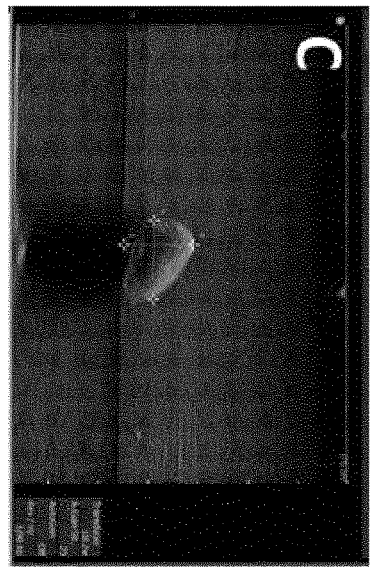
Figure 17:
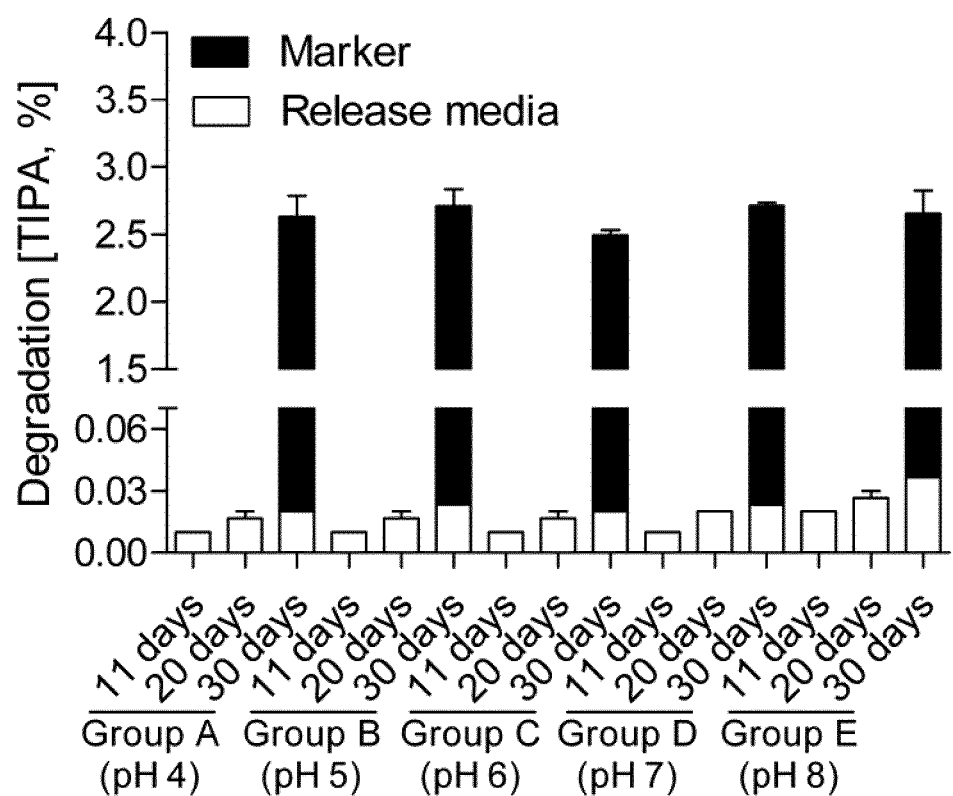
FIG. 17. Degradation of palpable markers at pH 4, 5, 6, 7 and 8 at 37° C.

The phantom containing the palpable markers were ultrasound scanned using a BK5000 Analogic ultrasound scanner equipped with a 10L2W transducer running at 7 MHz. Both palpable markers (100 μL and 300 μL) were clearly visible in ultrasonography in the breast equivalent phantom as illustrated in FIG. 16.

Example 12: Stability of Palpable Markers Vs. pH

The chemical stability of palpable markers with the composition listed in Table 8 were evaluated at pH 4, 5, 6, 7 and 8 to verify sufficient stability at all possible pH levels observed in viable and non-viable tissue.

TABLE 8

Specifications for preparation of Formulation #1

| | Composition (w/w %) | | | |
|---|---|---|---|---|
| Formulation# | LOIB | x-SAIB | EtOH | D&C Violet No. 2 |
| 1 | 51.9 | 30 | 18 | 0.10 |

Palpable markers (300 μL, n=3×5) were prepared from Formulation #1 by injection into glass vials (16 mL) containing MQ-H$_2$O (10 mL, ~50° C.) using a standard 1 mL disposable syringe with Luer-lock using a 25G needle.

Following marker injection, the markers were stored at 37° C. and the aqueous solution was discarded one day after marker injection and replaced with a 50 mM BIS-TRIS propane (pKa: 6.8 and 9.0) and Citric acid (pKa: 3.1, 4.8 and 6.4) buffer at pH 4, 5, 6, 7 or 8. Each group of markers were incubated at 37° C. for a period of 30 days the chemical stability evaluated by analytical HPLC based on a standard reference curve of 2-(2,4,6-triiodophenoxy) acetic acid (TIPA) and the known concentration of x-SAIB in the palpable markers as outlined below:

$$\text{Degradation (\%)} = \frac{m_{TIPA,H_2O} + m_{TIPA,marker}}{m_{TIPA,total}} * 100\%$$

Minimal degradation of the palpable markers (<3%) was observed over a period of 30 days at 37° C. at all pH levels tested supporting excellent chemical stability of the palpable markers.

The invention claimed is:

1. A palpable marker composition comprising non-water soluble carbohydrates, wherein at least 50% of the non-water soluble carbohydrates are carbohydrates selected from derivatives of saccharides with at least one pyranose or furanose saccharide unit, sucrose, lactose, maltose, trehalose, raffinose, glucosamine, galactosamine, lactosamine, or derivatives of disaccharides with at least one pyranose or furanose saccharide unit, or trisaccharides, or tetrasaccharides, or mixtures thereof, wherein the palpable marker composition comprises lactose octaisobutyrate (LOIB), and wherein the composition is a liquid before administration into the human or animal body, and:
   a) increases in viscosity by more than 50,000 centipoise (cP) after administration, for using the palpable marker composition for marking, identifying and/or locating a target tissue; or
   b) becomes a semi-crystaline, crystaline or amorphous solid after administration for using the palpable marker composition for marking, identifying and/or locating a target tissue.

2. The palpable marker composition according to claim 1, wherein the non-water soluble carbohydrates are selected from the group consisting of sucrose, lactose, maltose, trehalose, raffinose and derivatives of disaccharides with at least one pyranose unit.

3. The palpable marker composition according to claim 1, wherein the target tissue is selected from the group consisting of a non-palpable tumor, a palpable tumor, and a target needing to be surgically removed or destroyed.

4. The palpable marker composition according to claim 1, wherein the composition is a liquid before administration into the human or animal body that increases in viscosity by more than 500,000 centipoise (cP) after administration into the human or animal body.

5. The palpable marker composition according to claim 1, wherein the composition is a liquid before administration and has the ability to transform into a gel-like material after administration into the human or animal body due to diffusion of a molecule out of the administered material and into surrounding tissue.

6. The palpable marker composition according to claim 1, wherein the composition becomes a semi-crystalline, crystalline or amorphous solid by precipitation after administration into the human or animal body due to diffusion of a molecule out of the administered material and into surrounding tissue.

7. The palpable marker composition according to claim 1, wherein the increase in viscosity or precipitation after administration into the human or animal body is due to diffusion of solvent molecules out of the administered material and into the surrounding tissue.

8. The palpable marker composition according to claim 1, wherein the non-water soluble carbohydrates are disaccharides with structures selected from:

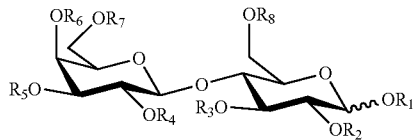

Formulae I

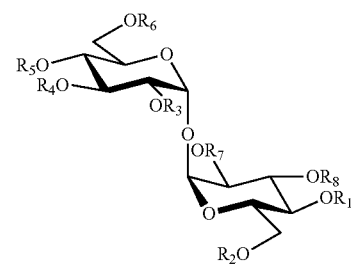

II

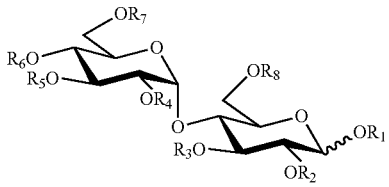

III wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

9. The palpable marker composition according to claim 1, wherein the non-water soluble carbohydrates are trisaccharides with structures selected from:

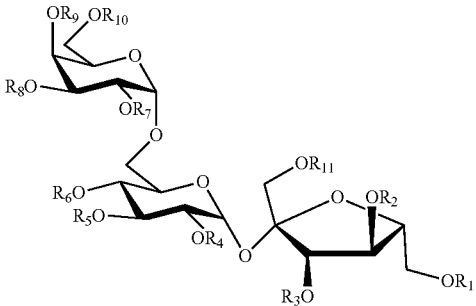

Formulae IV wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

10. The palpable marker composition according to claim 1 wherein at least 50% of the non-water soluble carbohydrates are mono- or oligosaccharides containing at least one amino sugar unit.

11. The palpable marker composition according to claim 10, wherein the amino sugar has the structure:

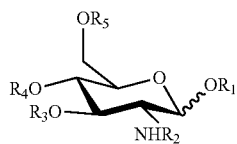

Formulae V wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, and mono-, di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of anomers such as α- and β-anomer centres of the above mentioned structural variations are claimed.

12. The palpable marker composition according to claim 1, wherein the composition comprises contrast agents that make the composition visible by PET imaging, SPECT imaging, Ultrasound imaging, x-ray imaging, fluorescence imaging, or OCT imaging.

13. The palpable marker composition according to claim 1, which is administered to the human or animal body through a syringe, an endoscope, a bronchoscope or a biopsy equipment to the target tissue.

14. The palpable marker composition according to claim 1 for local administration, wherein at least 60% of an administrated amount of marker remains more than 24 hours within 10 cm from an injection point when the palpable marker composition is administrated to a human or animal body.

15. A method for identifying and/or locating a non-palpable tumor or a target tissue needing to be surgically removed or destroyed, the method comprising injection of a palpable marker composition, wherein the palpable marker composition is injected in soft tissue comprising inserting needle means into the soft tissue, identifying the position of said needle means in said soft tissue, further inserting said needle means into said soft tissue until a needle tip of said needle means reaches said non palpable tumor, injecting palpable marker composition, wherein the palpable marker composition comprises non-water soluble carbohydrates, wherein at least 50% of the non-water soluble carbohydrates are carbohydrates selected from derivatives of sucrose, lactose, maltose, trehalose, raffinose, glucosamine, galactosamine, lactosamine, or derivatives of disaccharides with at least two pyranose saccharide units, or trisaccharides, or tetrasaccharides, or mixtures thereof, and wherein the composition is a liquid before administration into the human or animal body and a) increases in viscosity by more than 50,000 centipoise (cP) after administration, wherein the palpable marker composition is detectable by palpation; or b) becomes a semi-crystaline, crystaline or amorphous solid after administration, wherein the palpable marker composition is detectable by palpation.

16. The method according to claim 15, wherein the palpable marker composition stays within 10 cm from the site of injection, for at least several days, once it has been administered into the soft tissue of an animal or human body.

17. The method according to claim 15, wherein the palpable marker composition is detectable by X-ray imaging, computed tomography (CT) imaging, magnetic resonance imaging (MM), positron-emission tomography (PET) imaging, single photon emission computed tomography (SPECT) imaging, nuclear scintigraphy imaging, ultrasonography imaging, ultrasonic imaging, near-infrared imaging and/or fluorescence imaging.

18. The method according to claim 15, wherein the palpable marker composition is a liquid before administration into the human or animal body that increases in viscosity by more than 50,000 centipoise (cP) after administration into the human or animal body.

19. The method according to claim 15, wherein the palpable marker composition is a liquid before administration and has the ability to transform into a gel-like material after administration due to diffusion of a molecule out of the administered material and into surrounding tissue.

20. The method according to claim 15, wherein the palpable marker composition becomes a semi-crystalline, crystalline or amorphous solid by precipitation after administration, due to diffusion of a molecule out of the administered material and into surrounding tissue.

21. The method according to claim 15, wherein an increase in viscosity or precipitation of the palpable marker composition after administration into the human or animal body is due to diffusion of solvent molecule out of the administered material and into surrounding tissue.

22. A method for identifying and/or locating a non-palpable tumor or a target tissue needing to be surgically removed or destroyed, the method comprising administration of the palpable marker composition according to claim 1.

23. A kit of parts for identifying and locating a non-palpable tumor or a target tissue needing to be surgically removed or destroyed, the kit of parts comprising an injecting means and the palpable marker composition according to claim 1.

* * * * *